United States Patent [19]

Sum et al.

[11] Patent Number: 5,420,272
[45] Date of Patent: May 30, 1995

[54] 7-(SUBSTITUTED)-8-(SUBSTITUTED)-9-[(SUBSTITUTED GLYCYL)AMIDO]-6-DEMETHYL-6-DEOXYTETRACYCLINES

[75] Inventors: Phaik-Eng Sum, Pomona; Ving J. Lee, Monsey; Joseph J. Hlavka, Tuxedo Park, all of N.Y.; Raymond T. Testa, Cedar Grove, N.J.

[73] Assignee: American Cyanamid Company, Wayne, N.J.

[21] Appl. No.: 928,578

[22] Filed: Aug. 13, 1992

[51] Int. Cl.⁶ .................... C07C 231/12; C07C 233/64
[52] U.S. Cl. ........................................ 544/63; 544/336;
544/383; 544/404; 544/98; 544/88; 544/224;
544/106; 544/128; 544/235; 546/184; 546/112;
546/242; 548/452; 548/950; 548/954; 548/400;
548/967; 548/373.1; 548/375.1; 548/255;
548/262.2; 548/335.1; 548/250; 548/304.1
[58] Field of Search .................. 552/205; 544/63, 336,
544/383, 404, 98, 88, 224, 178, 235, 106;
546/184, 112, 242; 548/373.1, 375.1, 255, 262.2,
335.1, 250, 304.1, 343.5, 579, 361.1, 362.2, 207,
59, 950, 954, 400, 967; 549/68, 496, 505; 585/22

[56] References Cited

U.S. PATENT DOCUMENTS

| | | | |
|---|---|---|---|
| Re. 26,253 | 8/1967 | Petisi | 260/559 |
| Re. 26,271 | 9/1967 | Boothe | 260/559 |
| 2,482,055 | 9/1949 | Duggar . | |
| 3,007,965 | 11/1961 | Growich . | |
| 3,043,875 | 7/1962 | Beereboom . | |
| 3,200,149 | 8/1965 | Blackwood . | |
| 3,226,436 | 12/1965 | Petisi . | |
| 3,338,963 | 8/1967 | Petisi . | |
| 3,341,585 | 9/1967 | Bitha . | |
| 3,360,557 | 12/1967 | Shu . | |
| 3,360,561 | 12/1967 | Zambrano . | |
| 3,518,306 | 6/1970 | Martell . | |
| 3,829,453 | 8/1974 | Conover et al. | 552/205 |
| 5,021,407 | 6/1991 | Levy | 514/154 |

OTHER PUBLICATIONS

Chopra, Handbook of Experimental Parmacology, vol. 78, 317–392, Springer–Verlag (1985).
Levy, antimicrobial Agents and Chemotherapy, vol. 33, No. 8, 1373–1374, (Aug. 1989).
Salyers, Molecular Microbiology, 4(1), 151–156 (1990).

*Primary Examiner*—Marianne M. Cintins
*Assistant Examiner*—Kimberly J. Kestler
*Attorney, Agent, or Firm*—T. S. Szatkowski

[57] ABSTRACT

The invention provides compounds of the formula:

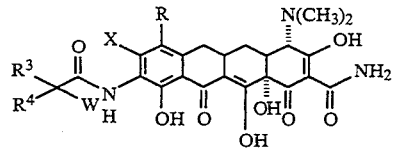

wherein R, $R^3$, $R^4$, X and W are defined in the specification. These compounds are useful as antibiotic agents.

51 Claims, No Drawings

7-(SUBSTITUTED)-8-(SUBSTITUTED)-9-](SUBSTITUTED GLYCYL)AMIDO]-6-DEMETHYL-6-DEOXYTETRACYCLINES

BACKGROUND OF THE INVENTION

Field of the Invention

The invention relates to novel [4S-(4alpha,-12alpha)]-4-(dimethylamino)-7-(substituted)-8-(substituted)-9-[[(substituted amino)substituted]amino]-1,4,4a,5,5a,6,11,12a-octahydro-3,10,12,12a-tetrahydroxy-1,11-dioxo-2-naphthacenecarboxamides, herein after called 7-(substituted)-8-(substituted)-9-[(substituted glycyl)amido]-6-demethyl-6-deoxytetracyclines, which exhibit antibiotic activity against a wide spectrum of organisms including organisms which are resistant to tetracyclines and are useful as antibiotic agents.

The invention also relates to novel 9-[(haloacyl)amido]-7-(substituted)-8-(substituted)-6-demethyl-6-deoxytetracycline intermediates useful for making the novel compounds of the present invention and to novel methods for producing the novel compounds and intermediate compounds.

SUMMARY OF THE INVENTION

This invention is concerned with novel 7-(substituted)-8-(substituted)-9-[(substituted glycyl)amido]-6-demethyl-6-deoxytetracyclines, represented by formula I and II, which have antibacterial activity; with method of treating infectious diseases in warm blooded animals employing these compounds; with pharmaceutical preparations containing these compounds; with novel intermediate compounds and processes for the production of these compounds. More particularly, this invention is concerned with compounds of formula I and II which have enhanced antibiotic activity against tetracycline resistant strains as well as a high level of activity against strains which are normally susceptible to tetracyclines.

and when $R^1$=methyl or ethyl, $R^2$=methyl, ethyl, n-propyl, 1-methylethyl, n-butyl, 1-methylpropyl or 2-methylpropyl;

and when $R^1$=n-propyl, $R^2$=n-propyl, 1-methylethyl, n-butyl, 1-methylpropyl or 2-methylpropyl;

and when $R^1$=1-methylethyl, $R^2$=n-butyl, 1-methylpropyl or 2-methylpropyl;

and when $R^1$=n-butyl, $R^2$=n-butyl, 1-methylpropyl or 2-methylpropyl;

and when $R^1$=1-methylpropyl, $R^2$=2-methylpropyl;

$R^3$ is selected from hydrogen; straight or branched ($C_1$–$C_8$)alkyl group selected from methyl, ethyl, propyl, isopropyl, butyl, isobutyl, pentyl, hexyl, heptyl and octyl; α-mercapto($C_1$–$C_4$)alkyl group selected from mercaptomethyl, α-mercaptoethyl, α-mercapto-1-methylethyl, α-mercaptopropyl and α-mercaptobutyl; α-hydroxy($C_1$–$C_4$)alkyl group selected from hydroxymethyl, α-hydroxyethyl, α-hydroxy-1-methylethyl, α-hydroxypropyl and α-hydroxybutyl; carboxyl($C_1$–$C_8$)alkyl group; ($C_6$–$C_{10}$)aryl group selected from phenyl, α-naphthyl and β-naphthyl; substituted($C_6$–$C_{10}$)aryl group (substitution selected from hydroxy, halogen, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino and carboxy); ($C_7$–$C_9$)aralkyl group selected from benzyl, 1-phenylethyl, 2-phenylethyl and phenylpropyl; substituted($C_7$–$C_9$)aralkyl group [substitution selected from halo, ($C_1$–$C_4$)alkyl, nitro, hydroxy, amino, mono- or disubstituted ($C_1$–$C_4$)alkylamino, ($C_1$–$C_4$)alkoxy, ($C_1$–$C_4$)alkylsulfonyl, cyano and carboxy];

$R^4$ is selected from hydrogen and ($C_1$–$C_6$)alkyl selected from methyl, ethyl propyl, isopropyl, butyl, isobutyl, pentyl and hexyl;

when $R^3$ does not equal $R^4$ the stereochemistry of the asymmetric carbon (i.e., the carbon bearing the W substituent) maybe be either the racemate (DL) or the individual enantiomers (L or D);

W is selected from amino; hydroxylamino; ($C_1$–$C_{12}$)

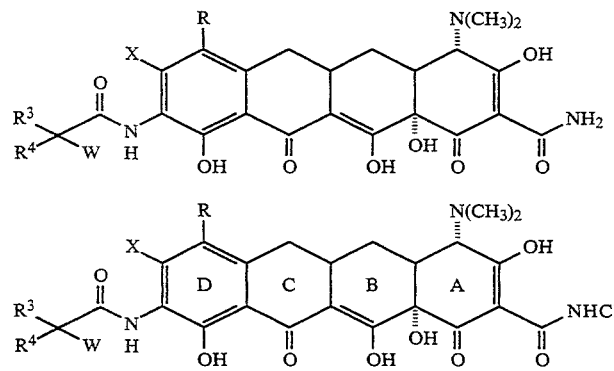

I

II

In formula I and II,

X is halogen or trifluoromethanesulfonyloxy, the halogen is selected from bromine, chlorine, fluorine and iodine;

R is selected from hydrogen; halogen selected from bromine, chlorine, fluorine and iodine; or $R=-NR^1R^2$ and when $R=-NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl;

straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl monosubstituted amino group; ($C_3$-$C_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl and bicyclo[2.2.2]oct-2-yl and the diastereomers and enantiomers of said ($C_3$-$C_8$)cycloalkyl monosubstituted amino; [($C_4$-$C_{10}$)cycloalkyl]alkyl monosubstituted amino group substitution selected from (cyclopropyl)methyl, (cyclopropyl)ethyl, (cyclobutyl)methyl, (trans-2-methylcyclopropyl)methyl, and (cis-2-methylcyclobutyl)methyl; ($C_3$-$C_{10}$)alkenyl monosubstituted amino group substitution selected from allyl, 3-butenyl, 2-butenyl(-cis or trans), 2-pentenyl, 4-octenyl, 2,3-dimethyl-2-butenyl, 3-methyl-2-butenyl, 2-cyclopentenyl and 2-cyclohexenyl; ($C_6$-$C_{10}$)aryl monosubstituted amino group substitution selected from phenyl and naphthyl; ($C_7$-$C_{10}$)aralkylamino group substitution selected from benzyl, 2-phenylethyl, 1-phenylethyl, 2-(naphthyl)methyl, 1-(naphthyl)methyl and phenylpropyl; substituted ($C_6$-$C_{10}$)aryl monosubstituted amino group [substitution selected from ($C_1$-$C_5$)acyl, ($C_1$-$C_5$)acylamino, ($C_1$-$C_4$)alkyl, mono or disubstituted ($C_1$-$C_8$)alkylamino, ($C_1$-$C_4$)alkoxy, ($C_1$-$C_4$)alkoxycarbonyl, ($C_1$-$C_4$)alkylsulfonyl, amino, carboxy, cyano, halogen, hydroxy, nitro and trihalo($C_1$-$C_3$)alkyl]; straight or branched symmetrical disubstituted ($C_2$-$C_{14}$)alkylamino group substitution selected from dimethyl, diethyl, diisopropyl, di-n-propyl, dibutyl and diisobutyl; symmetrical disubstituted ($C_3$-$C_{14}$)cycloalkylamino group substitution selected from dicyclopropyl, dicyclobutyl, dicyclopentyl, dicyclohexyl and dicycloheptyl; straight or branched unsymmetrical disubstituted ($C_3$-$C_{14}$)alkylamino group wherein the total number of carbons in the substitution is not more than 14; unsymmetrical disubstituted ($C_4$-$C_{14}$)cycloalkylamino group wherein the total number of carbons in the substitution is not more than 14; ($C_2$-$C_8$)azacycloalky and substituted ($C_2$-$C_8$)azacycloalkyl group substitution selected from aziridinyl, azetidinyl, pyrrolidinyl, piperdinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5yl, 2-azabicyclo[2.2.1]hept-2-yl, 7-azabicyclo[2.2.1]hept-7-yl, 2-azabicyclo[2.2.2]oct-2-yl and the diastereomers and enantiomers of said ($C_2$-$C_8$)azacycloalkyl and substituted ($C_2$-$C_8$)azacycloalkyl group; 1-azaoxacyloalkyl selected from morpholinyl and 1-aza-5-oxocycloheptaine; substitured 1-azaoxaycloalkyl group substitution selected from 2-($C_1$-$C_3$)alkylmorpholinyl, 3-($C_1$-$C_3$)alkylisoxazolidinyl, tetrahydrooxazinyl and 3,4-dihydrooxazinyl; [1,n]-diazacycloalkyl and substituted [1, n]-diazacycloalkyl group selected from piperazinyl, 2-($C_1$-$C_3$)alkylpiperazinyl, 4-($C_1$-$C_3$)alkylpiperazinyl, 2,4-dimethylpiperazinyl, 4-($C_1$-$C_4$)alkoxypiperazinyl, 4-($C_6$-$C_{10}$)aryloxypiperazinyl, 4-hydroxypiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, 2,5-diaza-5,7-dimethylbicyclo[2.2.2]oct-2-yl and the diastereomers or enantiomers of said [1,n]-diazacycloalkyl and substituted [1, n]-diazacycloalkyl group; 1-azathiacycloalkyl and substituted 1-azathiacycloalkyl group selected from thiomorpholinyl, 2-($C_1$-$C_3$)alkylthiomorpholinyl and 3-($C_3$-$C_6$)cycloalkylthiomorpholinyl; N-azolyl and substituted N-azolyl group selected from 1-imidazolyl, 2-($C_1$-$C_3$)alkyl-1-imidazolyl, 3-($C_1$-$C_3$)alkyl-1-imidazolyl, 1-pyrrolyl, 2-($C_1$-$C_3$)alkyl-1-pyrrolyl, 3-($C_1$-$C_3$)alkyl-1-pyrazolyl, indolyl, 1-(1,2,3-triazolyl), 4-($C_1$-$C_3$)alkyl-1-(1,2,3-triazolyl), 5-($C_1$-$C_3$)alkyl-1-(1,2,3-triazolyl), 4-(1,2,4-triazolyl, 1-tetrazolyl, 2-tetrazolyl and benzimidazolyl; (heterocycle)amino group selected from 2- or 3-furanylamino, 2- or 3-thienylamino, 2-, 3- or 4-pyridylamino, 2- or 5-pyridazinylamino, 2-pyrazinylamino, 2-(imidazolyl)amino, (benzimidazolyl)amino, and (benzothiazolyl)amino and substituted (heterocycle)amino group as defined above with substitution selected from straight or branched ($C_1$-$C_6$)alkyl; (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group as defined above with substitution selected from straight or branched ($C_1$-$C_6$)alkyl; carboxy($C_2$-$C_4$)alkylamino group selected from aminoacetic acid, α-aminopropionic acid, β-aminopropionic acid, α-butyric acid, and β-aminobutyric acid and the enantiomers of said carboxy($C_2$-$C_4$)alkylamino group; ($C_1$-$C_4$)alkoxycarbonylamino group substitution selected from methoxycarbonyl, ethoxycarbonyl, allyloxycarbonyl, propoxycarbonyl, isoproproxycarbonyl, 1,1-dimethylethoxycarbonyl, n-butoxycarbonyl, and 2-methylpropoxycarbonyl; ($C_1$-$C_4$)alkoxyamino group substitution selected from methoxy, ethoxy, n-propoxy, 1-methylethoxy, n-butoxy, 2-methylpropoxy, and 1,1-dimethylethoxy; ($C_3$-$C_8$)cycloalkoxyamino group selected from cyclopropoxy, trans-1,2-dimethylcyclopropoxy, cis-1,2-dimethylcyclopropoxy, cyclobutoxy, cyclopentoxy, cyclohexoxy, cycloheptoxy, cyclooctoxy, bicyclo[2.2.1]hept-2-yloxy, bicyclo[2.2.2]oct-2-yloxy and the diastereomers and enantiomers of said ($C_3$-$C_8$)cycloalkoxyamino group; ($C_6$-$C_{10}$)aryloxyamino group selected from phenoxyamino, 1-naphthyloxyamino and 2-naphthyloxyamino; ($C_7$-$C_{11}$)arylalkoxyamino group substitution selected from benzyloxy, 2-phenylethoxy, 1-phenylethoxy, 2-(naphthyl)methoxy, 1-(naphthyl)methoxy and phenylpropoxy;

$R^5$ is selected from hydrogen; straight or branched ($C_1$-$C_3$)alkyl group selected from methyl, ethyl, n-propyl or 1-methylethyl; ($C_6$-$C_{10}$)aryl group selected from phenyl, α-naphthyl or β-naphthyl; ($C_7$-$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

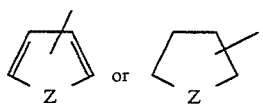

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

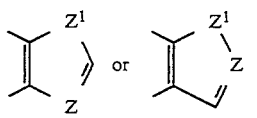

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

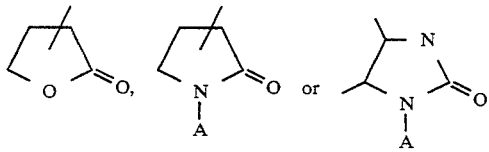

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —$(CH_2)_n COOR^7$ where n=0–4 and $R^7$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, or β-naphthyl;

$R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

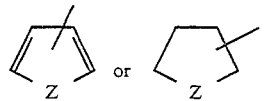

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

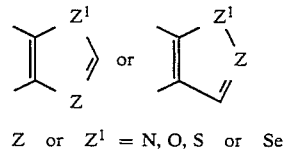

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

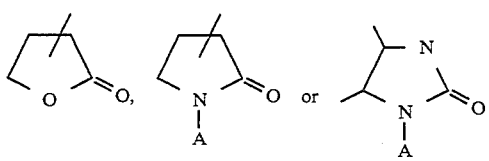

(A is selected from hydrogen; straight or branched ($C_1$–$C_4$)alkyl; $C_6$-aryl; substituted $C_6$-aryl (substitution selected from halo, ($C_1$–$C_4$)alkoxy, trihalo($C_1$–$C_3$)alkyl, nitro, amino, cyano, ($C_1$–$C_4$)alkoxycarbonyl, ($C_1$–$C_3$)alkylamino or carboxy); ($C_7$–$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-piperazinyl, 4-cyclopropyl-2-dioxo-1-piperazinyl, 2-dioxomorpholinyl, 2-dioxothiomorpholinyl; or —$(CH_2)_n COOR^7$ where n=0–4 and $R^7$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^5$ and $R^6$ cannot both be hydrogen;

or $R^5$ and $R^6$ taken together are —$(CH_2)_2B(CH_2)_2$—, wherein B is selected from $(CH_2)_n$ and n=0–1, —NH, —N($C_1$–$C_3$)alkyl [straight or branched], —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Preferred compounds are compounds according to the above formula I and II wherein: X is halogen or trifluoromethanesulfonyloxy, the halogen is selected from bromine, chlorine, fluorine and iodine; R is selected from hydrogen; halogen selected from bromine, chlorine and iodine; or R=—$NR^1R^2$ and when R=—$NR^1R^2$ and $R^1$=hydrogen, $R^2$=methyl, ethyl, n-propyl, 1-methylethyl, n-butyl, 1-methylpropyl or 2-methylpropyl;

and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched ($C_1$–$C_8$)alkyl group selected from methyl, ethyl, propyl, isopropyl, butyl, isobutyl, pentyl, hexyl, heptyl and octyl; α-hydroxy($C_1$–$C_4$)alkyl group selected from hydroxymethyl, α-hydroxyethyl, α-hydroxy-1-methylethyl, α-hydroxypropyl and α-hydroxybutyl; carboxyl($C_1$–$C_8$)alkyl group; ($C_6$–$C_{10}$)aryl group selected from phenyl, α-naphthyl and β-naphthyl; substituted ($C_6$–$C_{10}$)aryl group (substitution selected from hydroxy, halogen, ($C_1$–$C_4$)alkoxy, ($C_1$–$C_4$)alkoxycarbonyl, and carboxy); ($C_7$–$C_9$)aralkyl group selected from benzyl, 1-phenylethyl, 2-phenylethyl and phenylpropyl; substituted($C_7$–$C_9$)aralkyl group [substitution selected from halo, ($C_1$–$C_4$)alkyl, ($C_1$–$C_4$)alkoxy, ($C_1$–$C_4$)alkylsulfonyl, cyano and carboxy];

$R^4$ is selected from hydrogen and ($C_1$–$C_4$)alkyl selected from methyl, ethyl propyl, isopropyl, butyl and isobutyl;

when $R^3$ does not equal $R^4$ the stereochemistry of the asymmetric carbon (i.e., the carbon bearing the W substituent) maybe be either the racemate (DL) or the individual enantiomers (L or D);

W is selected from amino; hydroxylamino; ($C_1$–$C_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl and the diastereomers and enantiomers of said branched alkyl monosubstituted amino group; ($C_3$–$C_8$)cycloalkyl monosubstituted amino group substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, and the diastereomers and enantiomers of said ($C_3$–$C_8$)cycloalkyl monosubstituted amino group; [($C_4$–$C_{10}$)cycloalkyl]alkyl monosubstituted amino group substitution selected from (cyclopropyl)methyl, (cyclopropyl)ethyl, (cyclobutyl)methyl, (trans-2-methylcyclopropyl)methyl and (cis-2-methylcyclobutyl)methyl; ($C_3$–$C_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; ($C_7$–$C_{10}$)aralkylamino group substitution selected from benzyl, 2-phenylethyl, 1-phenylethyl, 2-(naphthyl)methyl, 1-(naphthyl)methyl and phenylpropyl; straight or branched symmetrical disubstituted ($C_2$–$C_{14}$)alkylamino group substitution selected from dimethyl, diethyl, diisopropyl, di-n-propyl, dibutyl and diisobutyl; symmetrical disubstituted ($C_3$–$C_{14}$)cycloalkylamino group substitution selected from dicyclopropyl, dicyclobutyl, dicyclopentyl, dicyclohexyl and dicycloheptyl; straight or branched unsymmetrical disubstituted ($C_3$–$C_{14}$)alkyl amino group wherein the total number of carbons in the substitution is not more than 14; unsymmetrical disubstituted ($C_4$–$C_{14}$)cycloalkylamino group wherein the total number of carbons in the substitution is not more than 14; ($C_2$–$C_8$)azacycloalkyl and substituted ($C_2$–$C_8$)azacycloalkyl group substitution selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, 2-azabicyclo[2.2.2]oct-2-yl and the diastereomers and enantiomers of said ($C_2$–$C_8$)azacycloalkyl and substituted ($C_2$–$C_8$)azacycloalkyl group; 1-azaoxacycloalkyl selected from morpholinyl and 1-aza-5-oxocycloheptane; substituted 1-azaoxacycloalkyl group substitution selected from 2-($C_1$–$C_3$)alkylmorpholinyl, 3-($C_1$–$C_3$)alkylisoxazolidinyl, tetrahydrooxazinyl and 3,4-dihydrooxazinyl; [1,n]-diazacycloalkyl and substituted [1,n]-diazacycloalkyl group selected from piperazinyl, 2-($C_1$–$C_3$)alkylpiperazinyl, 4-($C_1$–$C_3$)alkylpiperazinyl, 2,4-dimethylpiperazinyl, 4-($C_1$–$C_4$)alkoxypiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl, 2-($C_1$–$C_3$)alkylthiomorpholinyl and 3-($C_3$–$C_6$)cycloalkylthiomorpholinyl; N-azolyl and substituted N-azolyl group selected from 1-imidazolyl, 2-($C_1$–$C_3$)alkyl-1-imidazolyl, 3-($C_1$–$C_3$)alkyl-1-imidazolyl, 1-pyrrolyl, 2-($C_1$–$C_3$)alkyl-1-pyrrolyl, 3-($C_1$–$C_3$)alkyl-1-pyrazolyl, indolyl, 1-(1,2,3-triazolyl), 4-($C_1$–$C_3$)alkyl-1-(1,2,3-triazolyl), 5-($C_1$–$C_3$)alkyl-1-(1,2,3-triazolyl) and 4-(1,2,4-triazolyl); (heterocycle)methylamino group said heterocycle selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)amino group as defined above with substitution selected from straight or branched ($C_1$–$C_6$)alkyl; carboxy($C_2$–$C_4$)alkylamino group selected from aminoacetic acid, α-aminopropionic acid, β-aminopropionic acid, α-butyric acid, β-aminobutyric acid and the enantiomers of said carboxy($C_2$–$C_4$)alkylamino group; ($C_1$–$C_4$)alkoxycarbonylamino group substitution selected from methoxycarbonyl, ethoxycarbonyl, allyloxycarbonyl, propoxycarbonyl, isoproproxycarbonyl, 1,1-dimethylethoxycarbonyl, n-butoxycarbonyl, and 2-methylpropoxycarbonyl; ($C_1$-$C_4$)alkoxyamino group substitution selected from methoxy, ethoxy, n-propoxy, 1-methylethoxy, n-butoxy, 2-methylpropoxy, and 1,1-dimethylethoxy; ($C_3$-$C_8$)cycloalkoxyamino group selected from cyclopropoxy, trans-1,2-dimethylcyclopropoxy, cis-1,2-dimethylcyclopropoxy, cyclobutoxy, cyclopentoxy, cyclohexoxy, cycloheptoxy, cyclooctoxy, bicyclo[2.2.1]hept-2-yloxy, bicyclo[2.2.2]oct-2-yloxy and the diastereomers and enantiomers of said ($C_3$-$C_8$)cycloalkoxyamino group; ($C_7$-$C_{11}$)arylalkoxyamino group substitution selected from benzyloxy, 2-phenylethoxy, 1-phenylethoxy, 2-(naphthyl)methoxy, 1-(naphthyl)methoxy and phenylpropoxy;

$R^5$ is selected from hydrogen; straight or branched ($C_1$-$C_3$)alkyl group selected from methyl, ethyl, n-propyl or 1-methylethyl; ($C_6$-$C_{10}$)aryl group selected from phenyl, α-naphthyl or β-naphthyl; ($C_7$-$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

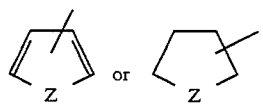

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

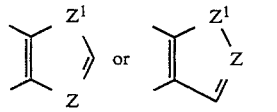

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3-alkyl-3H-imidazo[4,5-b]pyridyl or pyridylimidazolyl, or a five membered saturated ring with one or two N, O, S or Se heteroatoms and an adjacent appended O heteroatom:

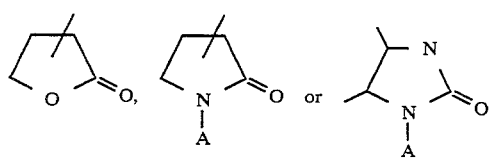

(A is selected from hydrogen; straight or branched ($C_1$-$C_4$)alkyl; $C_6$-aryl; ($C_7$-$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$-$C_3$)alkylthiopyridazinyl; or —$(CH_2)_n COOR^7$ where $n=0$-4 and $R^7$ is selected from hydrogen; straight or branched ($C_1$-$C_3$)alkyl group selected from methyl, ethyl, n-propyl or 1-methylethyl; or ($C_6$-$C_{10}$)aryl group selected from phenyl, α-naphthyl, or β-naphthyl;

$R^6$ is selected from hydrogen; straight or branched ($C_1$-$C_3$)alkyl group selected from methyl, ethyl, n-propyl or 1-methylethyl; ($C_6$-$C_{10}$)aryl group selected from phenyl, α-naphthyl or β-naphthyl; ($C_7$-$C_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

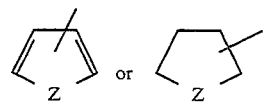

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

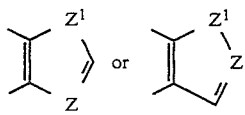

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom:

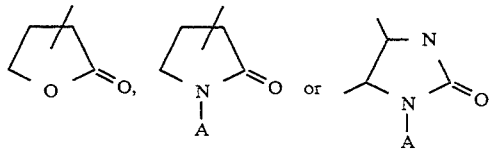

(A is selected from hydrogen; straight or branched ($C_1$-$C_4$)alkyl; $C_6$-aryl; ($C_7$-$C_9$)aralkyl group selected from benzyl, 1-phenylethyl, 2-phenylethyl or phenylpropyl) such as γ-butyrolactam, γ-butyrolactone, imidazolidinone or N-aminoimidazolidinone, or a six membered aromatic ring with one to three N heteroatoms such as pyridyl, pyridazinyl, pyrazinyl, sym-triazinyl, unsym-triazinyl, pyrimidinyl or ($C_1$-$C_3$)alkylthiopyridazinyl; or —(CH$_2$)$_n$COOR$^7$ where n=0–4 and R$^7$ is selected from hydrogen; straight or branched (C$_1$–C$_3$)alkyl selected from methyl, ethyl, n-propyl or 1-methylethyl; or (C$_6$–C$_{10}$)aryl selected from phenyl, α-naphthyl or β-naphthyl; with the proviso that R$^5$ and R$^6$ cannot both be hydrogen; or R$^5$ and R$^6$ taken together are —(CH$_2$)$_2$B(CH$_2$)$_2$—, wherein B is selected from (CH$_2$)$_n$ and n=0–1, —NH, —N(C$_1$–C$_3$)alkyl [straight or branched], —N(C$_1$–C$_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Particularly preferred compounds are compounds according to the above formula I and II wherein:

X is halogen or trifluoromethanesulfonyloxy, the halogen is selected from bromine, chlorine, fluorine and iodine; R is selected from hydrogen; halogen selected from bromine, chlorine and iodine; or R=—NR$^1$R$^2$ and when R=—NR$^1$R$^2$ and R$^1$=hydrogen, R$^2$=methyl, ethyl, n-propyl, 1-methylethyl, n-butyl, 1-methylpropyl, 2-methylpropyl or 1,1-dimethylethyl;

and when R$^1$=methyl or ethyl, R$^2$=methyl, ethyl, n-propyl, 1-methylethyl, n-butyl, 1-methylpropyl or 2-methylpropyl;

R$^3$ is selected from hydrogen; straight or branched (C$_1$–C$_6$)alkyl group selected from methyl, ethyl, propyl, isopropyl, butyl, isobutyl, pentyl and hexyl; (C$_6$–C$_{10}$)aryl group selected from phenyl, α-naphthyl and β-naphthyl; (C$_7$–C$_9$)aralkyl group selected from benzyl, 1-phenylethyl, 2-phenylethyl and phenylpropyl;

R$^4$ is selected from hydrogen and (C$_1$–C$_4$)alkyl selected from methyl, ethyl propyl, isopropyl, butyl and isobutyl;

when R$^3$ does not equal R$^4$ the stereochemistry of the asymmetric carbon (i.e., the carbon bearing the W substituent) maybe be either the racemate (DL) or the individual enantiomers (L or D);

W is selected from amino; (C$_1$–C$_{12}$) straight or branched alkyl monosubstituted amino group substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl and the diastereomers and enantiomers of said branched alkyl monosubstituted amino group; (C$_3$–C$_5$)cycloalkyl monosubstituted amino group substitution selected from cyclopropyl, trans-1,2-dimethylcyclopropyl, cis-1,2-dimethylcyclopropyl, cyclobutyl and the diastereomers and enantiomers of said (C$_3$–C$_5$)cycloalkyl monosubstituted amino group; [(C$_4$–C$_{10}$)cycloalkyl]alkyl monosubstituted amino group substitution selected from (cyclopropyl)methyl, (cyclopropyl)ethyl and (cyclobutyl)methyl; (C$_3$–C$_{10}$)alkenyl monosubstituted amino group substitution selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; (C$_7$–C$_{10}$)aralkylamino group substitution selected from benzyl, 2-phenylethyl, 1-phenylethyl, 2-(naphthyl)methyl, 1-(naphthyl)methyl and phenylpropyl;

straight or branched symmetrical disubstituted (C$_2$–C$_{14}$)alkylamino group substitution selected from dimethyl, diethyl, diisopropyl, and di-n-propyl; straight or branched unsymmetrical disubstituted (C$_3$–C$_{14}$)alkylamino group wherein the total number of carbons in the substitution is no more than 14; unsymmetrical disubstituted (C$_4$–C$_{14}$)cycloalkylamino group wherein the total number of carbons in the substitution is no more than 14; (C$_2$–C$_8$)azacycloalkyl and substituted (C$_2$–C$_8$)azacycloalkyl group substitution selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl and the diastereomers and enantiomers of said (C$_2$–C$_8$)azacycloalkyl and substituted (C$_2$–C$_8$)azacycloalkyl group; 1-azaoxacycloalkyl selected from morpholinyl and 1-aza-5-oxocycloheptane; substituted 1-azaoxacycloalkyl group substitution selected from 2-(C$_1$–C$_3$)alkylmorpholinyl, 3-(C$_1$–C$_3$)alkylisoxazolidinyl and tetrahydrooxazinyl; [1,n]-diazacycloalkyl and substituted [1,n]-diazacycloalkyl group selected from piperazinyl, 2-(C$_1$–C$_3$)alkylpiperazinyl, 4-(C$_1$–C$_3$)alkylpiperazinyl, 2,4-dimethylpiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl and 2-(C$_1$–C$_3$)alkylthiomorpholinyl; N-azolyl and substituted N-azolyl group selected from 1-imidazolyl, indolyl, 1-(1,2,3-triazolyl) and 4-(1,2,4-triazolyl); (heterocycle)methylamino group selected from 2- or 3-furylmethylamino, 2- or 3-thienylmethylamino and 2-, 3- or 4-pyridylmethylamino; (C$_1$–C$_4$)alkoxycarbonylamino group substitution selected from methoxycarbonyl, ethoxycarbonyl, allyloxycarbonyl, propoxycarbonyl, isoproproxycarbonyl, 1,1-dimethylethoxycarbonyl, n-butoxycarbonyl, and 2-methylpropoxycarbonyl; (C$_1$–C$_4$)alkoxyamino group substitution selected from methoxy, ethoxy, n-propoxy, 1-methylethoxy, n-butoxy, 2-methylpropoxy, and 1,1-dimethylethoxy; (C$_7$–C$_{11}$)arylalkoxyamino group substitution selected from benzyloxy, 2-phenylethoxy, 1-phenylethoxy, 2-(naphthyl)methoxy, 1-(naphthyl)methoxy and phenylpropoxy;

R$^5$ is selected from hydrogen; straight or branched (C$_1$–C$_3$)alkyl group selected from methyl, ethyl, n-propyl or 1-methylethyl; (C$_6$–C$_{10}$)aryl group selected from phenyl, α-naphthyl or β-naphthyl; (C$_7$–C$_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

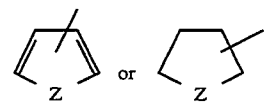

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

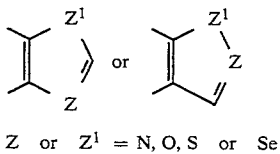

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; or —(CH$_2$)$_n$COOR$^7$ where n=0–4 and R$^7$ is selected from hydrogen; straight or branched (C$_1$–C$_3$)alkyl group selected from methyl, ethyl, n-propyl or 1-methylethyl; or (C$_6$–C$_{10}$)aryl group selected from phenyl, α-naphthyl, or β-naphthyl;

R$^6$ is selected from hydrogen; straight or branched (C$_1$–C$_3$)alkyl group selected from methyl, ethyl, n-propyl or 1-methylethyl; (C$_6$–C$_{10}$)aryl group selected from phenyl, α-naphthyl or β-naphthyl; (C$_7$–C$_9$)aralkyl group such as benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto:

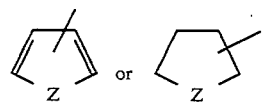

Z = N, O, S or Se such as pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto:

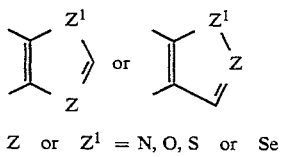

Z or $Z^1$ = N, O, S or Se such as imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; or —(CH$_2$)$_n$COOR$^7$ where n=0–4 and R$^7$ is selected from hydrogen; straight or branched (C$_1$–C$_3$)alkyl selected from methyl, ethyl, n-propyl or 1-methylethyl; or (C$_6$–C$_{10}$)aryl selected from phenyl, α-naphthyl or β-naphthyl; with the proviso that R$^5$ and R$^6$ cannot both be hydrogen; or R$^5$ and R$^6$ taken together are —(CH$_2$)$_2$B(CH$_2$)$_2$—, wherein B is selected from (CH$_2$)$_n$ and n=0–1, —NH, —N(C$_1$–C$_3$)alkyl [straight or branched], —N(C$_1$–C$_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Compounds of special interest are compounds according to the above formula I and II wherein: X is halogen or trifluoromethanesulfonyloxy, the halogen is selected from chlorine and fluorine; R is selected from hydrogen; halogen selected from chlorine and iodine; or R=—NR$^1$R$^2$ and when R=—NR$^1$R$^2$ and R$^1$=methyl or ethyl, R$^2$=methyl and ethyl;

R$^3$ is selected from hydrogen; straight or branched (C$_1$–C$_2$)alkyl group selected from methyl and ethyl; R$^4$ is selected from hydrogen and (C$_1$–C$_6$)alkyl selected from methyl and ethyl;

when R$^3$ does not equal R$^4$ the stereochemistry of the asymmetric carbon (i.e., the carbon bearing the W substituent) maybe be either the racemate (DL) or the individual enantiomers (L or D);

W is selected from amino; (C$_1$–C$_4$)straight or branched alkyl monosubstituted amino group substitution selected from methyl, ethyl, n-propyl, 1-methylethyl, n-butyl and 1-methylpropyl; (C$_3$–C$_4$)cycloalkyl monosubstituted amino group substitution selected from cyclopropyl and cyclobutyl; (C$_2$–C$_8$)azacycloalkyl and substituted (C$_2$–C$_8$)azacycloalkyl selected from pyrrolidinyl, piperidinyl and 4-methylpiperidinyl; 1-azaoxacycloalkyl selected from morpholinyl; [1,n]-diazacycloalkyl and substituted [1,n]-diazacycloalkyl group selected from piperazinyl and 4-(C$_1$–C$_3$)alkylpiperazinyl; N-azolyl and substituted N-azolyl group selected from 1-imidazolyl, 2-(C$_1$–C$_3$)alkyl-1-imidazolyl and 3-(C$_1$–C$_3$)alkyl-1-imidazolyl; (heterocycle)methylamino group said heterocycle selected from 2-, 3- or 4-pyridylmethylamino; carboxy(C$_2$–C$_4$)alkylamino group selected from aminoacetic acid, α-aminopropionic acid, β-aminopropionic acid, α-butyric acid, β-aminobutyric acid and the enantiomers of said carboxy(C$_2$–C$_4$)alkylamino group;

R$^5$ is selected from hydrogen; straight or branched (C$_1$–C$_3$)alkyl group selected from methyl, ethyl, n-propyl or 1-methylethyl;

R$^6$ is selected from hydrogen; straight or branched (C$_1$–C$_3$)alkyl group selected from methyl, ethyl, n-propyl or 1-methylethyl; with the proviso that R$^5$ and R$^6$ cannot both be hydrogen; or R$^5$ and R$^6$ taken together are —(CH$_2$)$_2$B(CH$_2$)$_2$—, wherein B is selected from (CH$_2$)$_n$ and n=0–1, —NH, —N(C$_1$–C$_3$)alkyl [straight or branched], —N(C$_1$–C$_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

Also included in the present invention are compounds useful as intermediates for producing the above compounds of formula I and II. Such intermediates include those having the formula III:

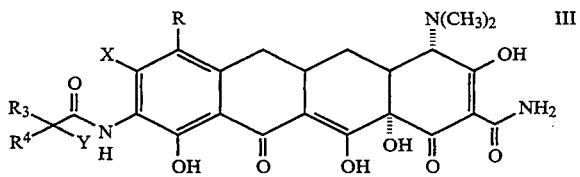

wherein:

Y is selected from $(CH_2)_nX'$, n=0–5, X' is halogen selected from bromine, chlorine, fluorine and iodine; X is halogen or trifluoromethanesulfonyl, the halogen is selected from bromine, chlorine, fluorine and iodine. R is selected from hydrogen; halogen selected from bromine, chlorine, fluorine and iodine; or $R=-NR^1R^2$ and when $R=-NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl;

and when $R^1$=methyl or ethyl, $R^2$=methyl, ethyl, n-propyl, 1-methylethyl, n-butyl, 1-methylpropyl or 2-methylpropyl;

and when $R^1$=n-propyl, $R^2$=n-propyl, 1-methylethyl, n-butyl, 1-methylpropyl or 2-methylpropyl;

and when $R^1$=1-methylethyl, $R^2$=n-butyl, 1-methylpropyl or 2-methylpropyl;

and when $R^1$=n-butyl, $R^2$=n-butyl, 1-methylpropyl or 2-methylpropyl;

and when $R^1$=1-methylpropyl, $R^2$=2-methylpropyl;

$R^3$ is selected from hydrogen; straight or branched $(C_1-C_8)$alkyl group selected from methyl, ethyl, propyl, isopropyl, butyl, isobutyl, pentyl, hexyl, heptyl and octyl; α-mercapto$(C_1-C_4)$alkyl group selected from mercaptomethyl, α-mercaptoethyl, α-mercapto-1-methylethyl, α-mercaptopropyl and α-mercaptobutyl; α-hydroxy$(C_1-C_4)$alkyl group selected from hydroxymethyl, α-hydroxyethyl, α-hydroxy-1-methylethyl, α-hydroxypropyl and α-hydroxybutyl; carboxyl$(C_1-C_8)$alkyl group; $(C_6-C_{10})$aryl group selected from phenyl, α-naphthyl and β-naphthyl; substituted$(C_6-C_{10})$aryl group (substitution selected from hydroxy, halogen, $(C_1-C_4)$alkoxy, trihalo$(C_1-C_3)$alkyl, nitro, amino, cyano, $(C_1-C_4)$alkoxycarbonyl, $(C_1-C_3)$alkylamino and carboxy); $(C_7-C_9)$aralkyl group selected from benzyl, 1-phenylethyl, 2-phenylethyl and phenylpropyl; substituted$(C_7-C_9)$aralkyl group [substitution selected from halo, $(C_1-C_4)$alkyl, nitro, hydroxy, amino, mono- or disubstituted $(C_1-C_4)$alkylamino, $(C_1-C_4)$alkoxy, $(C_1-C_4)$alkylsulfonyl, cyano and carboxy];

$R^4$ is selected from hydrogen and $(C_1-C_6)$alkyl selected from methyl, ethyl propyl, isopropyl, butyl, isobutyl, pentyl and hexyl;

when $R^3$ does not equal $R^4$ the stereochemistry of the asymmetric carbon (i.e., the carbon bearing the W substituent) maybe be either the racemate (DL) or the individual enantiomers (L or D); and the pharmaco logically acceptible organic and inorganic salts or metal complexes.

Preferred compounds are compounds according to the above formula III wherein:

Y is selected from $(CH_2)_nX'$, n=0–5, X' is halogen selected from bromine, chlorine, flourine and iodine; X is halogen or trifluoromethanesulfonyloxy, the halogen is selected from bromine, chlorine, fluorine and iodine;

R is selected from hydrogen; halogen selected from bromine, chlorine and iodine; or $R=-NR^1R^2$ and when $R=-NR^1R^2$ and $R^1$=hydrogen, $R^2$=methyl, ethyl, n-propyl, 1-methylethyl, n-butyl, 1-methylpropyl or 2-methylpropyl;

and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched $(C_1-C_8)$alkyl group selected from methyl, ethyl, propyl, isopropyl, butyl, isobutyl, pentyl, hexyl, heptyl and octyl; α-hydroxy$(C_1-C_4)$alkyl group selected from hydroxymethyl, α-hydroxyethyl, α-hydroxy-1-methylethyl, α-hydroxypropyl and α-hydroxybutyl; carboxyl$(C_1-C_8)$alkyl group; $(C_6-C_{10})$aryl group selected from phenyl, α-naphthyl and β-naphthyl; substituted$(C_6-C_{10})$aryl group (substitution selected from hydroxy, halogen, $(C_1-C_4)$alkoxy, $(C_1-C_4)$alkoxycarbonyl, and carboxy); $(C_7-C_9)$aralkyl group selected from benzyl, 1-phenylethyl, 2-phenylethyl and phenylpropyl; substituted-$(C_7-C_9)$aralkyl group [substitution selected from halo, $(C_1-C_4)$alkyl, $(C_1-C_4)$alkoxy, $(C_1-C_4)$alkylsulfonyl, cyano and carboxy];

$R^4$ is selected from hydrogen and $(C_1-C_4)$alkyl selected from methyl, ethyl propyl, isopropyl, butyl and isobutyl;

when $R^3$ does not equal $R^4$ the stereochemistry of the asymmetric carbon (i.e., the carbon bearing the W substituent) maybe be either the racemate (DL) or the individual enantiomers (L or D); and the pharmacologically acceptible organic and inorganic salts or metal complexes.

Particularly preferred compounds are compounds according to the above formula III wherein:

Y is selected from $(CH_2)_nX'$, n=0–5, X' is halogen selected from bromine, chlorine, fluorine and iodine;

X is halogen or trifluoromethanesulfonyloxy, the halogen is selected from bromine, chlorine, fluorine and iodine;

R is selected from hydrogen; halogen selected from bromine, chlorine and iodine; or $R=-NR^1R^2$ and when $R=-NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl;

and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched $(C_1-C_6)$alkyl group selected from methyl, ethyl, propyl, isopropyl, butyl, isobutyl, pentyl and hexyl; $(C_6-C_{10})$aryl group selected from phenyl, α-naphthyl and β-naphthyl; $(C_7-C_9)$aralkyl group selected from benzyl, 1-phenylethyl, 2-phenylethyl and phenylpropyl;

$R^4$ is selected from hydrogen and $(C_1-C_4)$alkyl selected from methyl, ethyl propyl, isopropyl, butyl and isobutyl;

when $R^3$ does not equal $R^4$ the stereochemistry of the asymmetric carbon (i.e., the carbon bearing the W substituent) maybe be either the racemate (DL) or the individual enantiomers (L or D); and the pharmacologically acceptible organic and inorganic salts or metal complexes.

Compounds of special interest are compounds according to the above formula III wherein:

Y is selected from $(CH_2)_nX'$, $n=0-5$, $X'$ is halogen selected from bromine, chlorine, flourine and iodine;

X is halogen or trifluoromethanesulfonyloxy, the halogen is selected from chlorine and fluorine; R is selected from hydrogen; halogen selected from chlorine and iodine; or $R=-NR^1R^2$ and when $R=-NR^1R^2$ and $R^1=$methyl or ethyl, $R^2=$methyl and ethyl;

$R^3$ is selected from hydrogen; straight or branched $(C_1-C_2)$alkyl group selected from methyl and ethyl; $R^4$ is selected from hydrogen and $(C_1-C_6)$alkyl selected from methyl and ethyl;

when $R^3$ does not equal $R^4$ the stereochemistry of the asymmetric carbon (i.e., the carbon bearing the W substituent) maybe be either the racemate (DL) or the individual enantiomers (L or D); and the pharmacologically acceptible organic and inorganic salts or metal complexes.

DESCRIPTION OF THE PREFERRED EMBODIMENTS

The novel compounds of the present invention may be readily prepared in accordance with the following schemes.

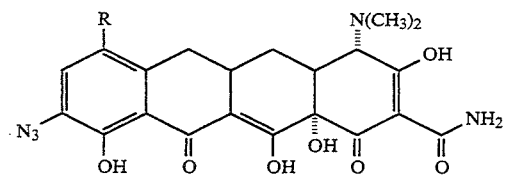

1a. $R=NR^2R^3$, $R^2=R^3$
1b. $R=NR^2R^3$, $R^2\neq R^3$
1c. $R=X$, $X=$halogen, hydrogen The starting 9-azido-7-(substituted)-6-demethyl-6-deoxytetracycline, 1, described in formula 1 is prepared according to Scheme I.

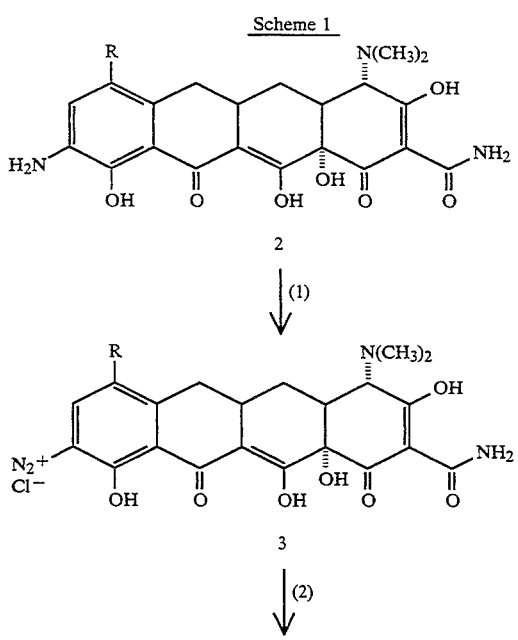

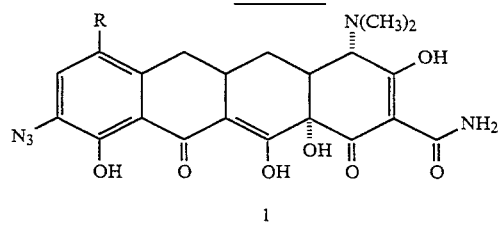

Reagents
(1) BuONO$_2$
   0.1N CH$_3$OH/HCl
(2) NaN$_3$
   0.1N CH$_3$OH/HCl

In accordance with Scheme I, 9-amino-7-(substituted)-6-demethyl-6-deoxytetracycline 2, or the mineral acid or halide salt, dissolved in 0.1N methanolic hydrogen chloride, is treated for from 5 minutes to 8 hours at from $-20°$ C. to $+45°$ C. with an excess of n-butyl nitrite to give a 9-diazonium-7-(substituted)-6-demethyl-6-deoxytetracycline, 3, or the mineral acid or halide salt. The formed diazonium compound, 3, or the mineral acid or halide salt, dissolved in 0.1N methanolic hydrogen chloride, is treated for 5 minutes to 8 hours at from $-5°$ C. to $+50°$ C. with one equivalent of sodium azide to give the corresponding 9-azido-7-(substituted)-6-demethyl-6-deoxytetracycline, 1, or the mineral acid or halide salt.

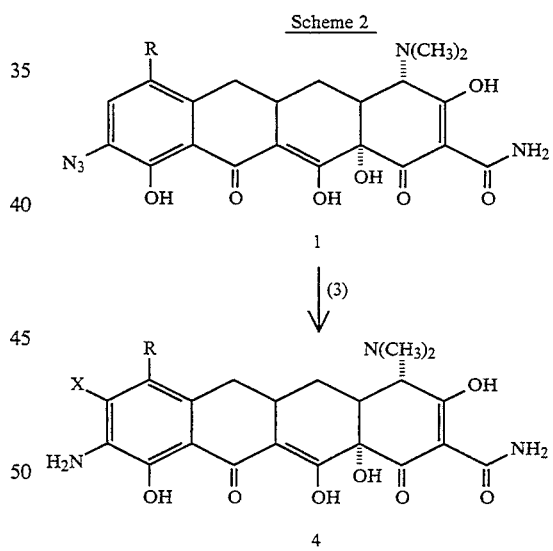

3. Strong acid
   (HCl, H$_2$SO$_4$, CF$_3$SO$_3$H, CH$_3$SO$_3$H, HI, HF and HBr)

In accordance with Scheme II, a 9-azido-7-(substituted)-6-demethyl-6-deoxytetracycline, 1, or the mineral acid or halide salt, is treated for from 5 minutes to 12 hours at from $-5°$ C. to 40° C. with a strong acid, such as sulfuric acid, hydrochloric acid, methanesulfonic acid, trifluoromethanesulfonic acid, hydrobromic, hydroiodic, or hydrogen fluoride to produce a 9-amino-7-(substituted)-8(substituted)-6-demethyl-6-deoxytetracycline, 4, or the mineral acid or halide salt.

The 9-amino-7-(substituted)-8-(substituted)-6-demethyl-6-deoxytetracycline, 4, or the mineral acid or halide salt, can be further converted as described in Scheme III.

tetrahydro-2(1H)pyrimidinone, 1,2-dimethoxyethane or equivalent thereof.

Scheme 3

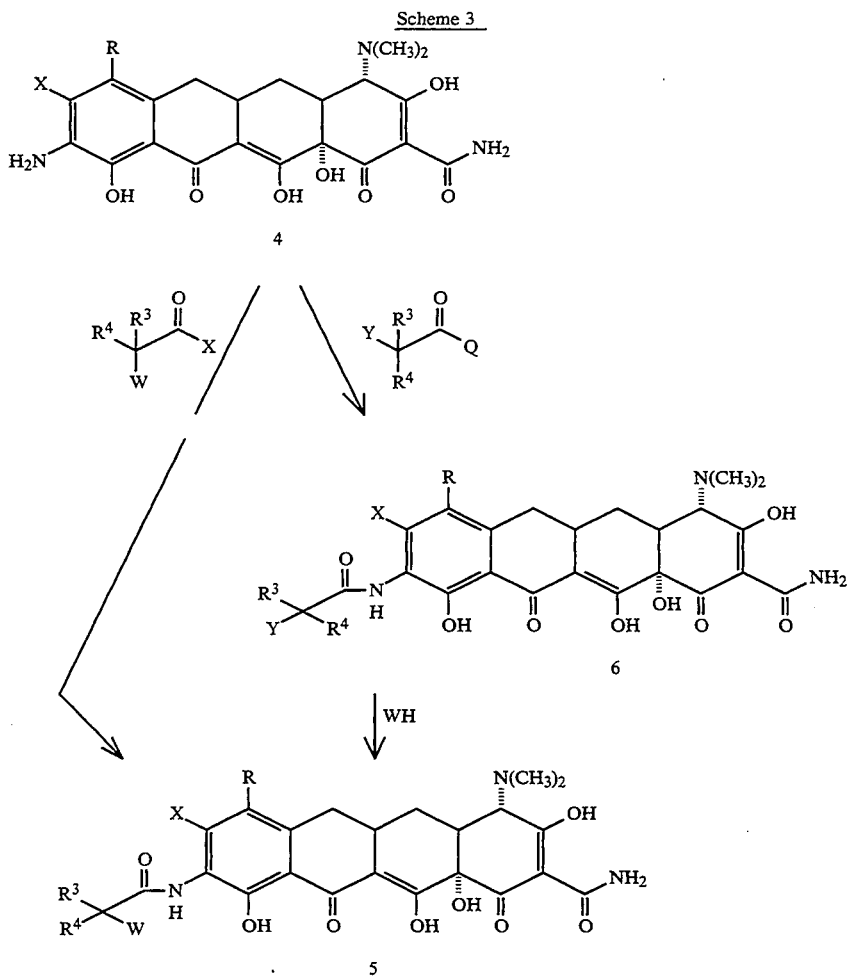

Y = (CH₂)ₙX', n = 0-5
X and Q = Cl, Br, I and F

In accordance with Scheme III, a 9-amino-7-(substituted)-8-(substituted)-6-demethyl-6-deoxytetracycline, 4, or the mineral acid or halide salt, is treated at room temperature for from 0.5-2 hours with an acid chloride of the formula:

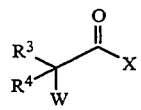

wherein R³, R⁴, W and X are defined hereinabove; in the presence of a suitable acid scavenger, in a suitable solvent, to form the corresponding 9-[(substituted glycyl)amido]-7-(substituted)-8-(substituted)-6-demethyl-6-deoxytetracycline, 5, or the mineral acid or halide salt.

The acid scavenger is selected from sodium bicarbonate, sodium acetate, pyridine, triethylamine, N,O-bis(-trimethylsilyl)acetamide, N,O-bis(trimethylsilyl)trifluoroacetamide, potassium carbonate, a basic ion exchange resin or equivalent thereof.

The solvents are selected from water, tetrahydrofuran, N-methylpyrrolidone, 1,3-dimethyl-2-imidazolidinone, hexamethylphosphoramide, 1,3-dimethyl-3,4,5,6-

Alternatively, in accordance with Scheme III, 9-amino-7-(substituted)-8-(substituted)-6-demethyl-6-deoxytetracycline, 4, or the mineral acid or halide salt, is treated with a straight or branched chain α-haloacyl halide of the formula:

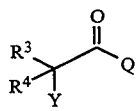

wherein R³, R⁴ and Y are defined hereinabove and Q is halogen selected from bromine, chlorine, fluorine and iodine, such as bromoacetyl bromide, chloroacetyl chloride, 2-bromopropionyl bromide or equivalent thereof; in the presence of a suitable acid scavenger, in a suitable of solvent, to form the corresponding 9-[(haloacyl)amido]-7-(substituted)-8-(substituted)-6-demethyl-6-deoxytetracycline, 6, or the mineral acid or halide salt.

The halogen, Y, and halide, Q, in the haloacyl halide can be the same or different halogen and are selected from bromine, chlorine, iodine and fluorine; Y is (CH₂)ₙX', n=0-5 and X' is a halogen.

The acid scavenger and suitable solvent are as defined hereinabove.

The 9-[(haloacyl)amido]-7-(substituted)-8-(substituted)-6-demethyl-6-deoxytetracycline, 6, or mineral acid or halide salt, is treated, under an inert atmosphere of nitrogen, argon or helium, with nucleophiles of the formula, WH, where W is defined hereinabove, such as amines or substituted amines or equivalents thereof, in a suitable solvent to form the corresponding 9-[(substituted glycyl)amido]-7-(substituted)-8-(substituted)-6-demethyl-6-deoxytetracycline, 5, or mineral acid or halide salt.

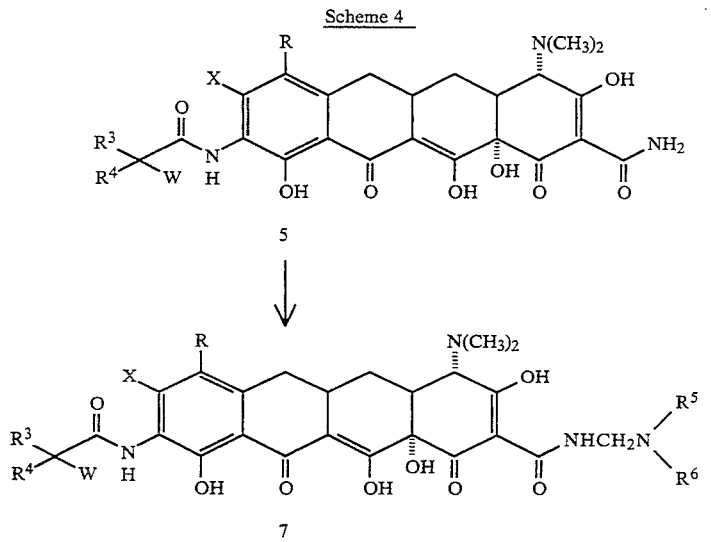

In accordance with Scheme IV, compound 5 is selectively N-alkylated in the presence of formaldehyde and either a primary amine of the formula $R^5NH_2$ such as methylamine, ethylamine, benzylamine, methyl glycinate, (L or D)lysine, (L or D)alanine or their substituted congeners; or a secondary amine of the formula $R^5R^6NH$ such as morpholine, pyrrolidine, piperidine or their substituted congeners to give the corresponding Mannich base adduct, 7.

The 9-[(substituted glycyl)amido]-7-(substituted)-8-(substituted)-6-demethyl-6-deoxytetracyclines may be obtained as metal complexes such as aluminum, calcium, iron, magnesium, manganese and complex salts; inorganic and organic salts and corresponding Mannich base adducts using methods known to those skilled in the art (Richard C. Larock, Comprehensive Organic Transformations, VCH Publishers, 411–415, 1989). Preferably, the 7-(substituted)-8-(substituted)-9-(substituted)-6-demethyl-6-deoxytetracyclines are obtained as inorganic salts such as hydrochloric, hydrobromic, hydroiodic, phosphoric, nitric or sulfate; or organic salts such as acetate, benzoate, citrate, cysteine or other amino acids, fumarate, glycolate, maleate, succinate, tartrate, alkylsulfonate or arylsulfonate. Depending on the stoichiometry of the acids used, the salt formation occurs with the C(4)-dimethylamino group (1 equivalent of acid) or with both the C(4)-dimethylamino or the W group (2 equivalents of acid). The salts are preferred for oral and parenteral administration.

Some of the compounds of the hereinbefore described Schemes have centers of asymmetry at the carbon bearing the W substituent. The compounds may, therefore, exist in at least two (2) stereoisomeric forms. The present invention encompasses all stereoisomers of the compounds whether free from other stereoisomers or admixed with stereoisomers in any proportion of enantiomers. The absolute configuration of any compound may be determined by conventional X-ray crystallography.

The stereochemistry centers on the tetracycline unit (i.e., C-4, C-4a, C-5a and C-12a) remain intact throughout the reaction sequences.

BIOLOGICAL ACTIVITY

Methods for in Vitro antibacterial evaluation (Table I)

The minimum inhibitory concentration (MIC), the lowest concentration of the antibiotic which inhibits growth of the test organism, is determined by the agar dilution method using 0.1 ml Muller-Hinton II agar (Baltimore Biological Laboratories) per well. An inoculum level of $1-5 \times 10^5$ CFU/ml, and a range of antibiotic concentrations (32–0.004 microgram/ml) is used. MIC is determined after the plates are incubated for 18 hours at 35° C. in a forced air incubator. The test organisms comprise genetically defined strains that are sensitive to tetracycline and resistant strains that are insensitive to tetracycline, either by preventing the antibiotic from interacting with bacterial ribosomes (tetM) or by a tetK encoded membrane protein which confers tetracycline resistance by energy-dependent efflux of the antibiotic from the cell.

Testing Results

The claimed compounds exhibit antibacterial activity against a spectrum of tetracycline sensitive and resistant Gram-positive and Gram-negative bacteria, especially, strains of *E. coli, S. aureus* and *E. faecalis*, containing the tetM resistance determinants (Table I). Notable is 8-chloro-9-(N,N-dimethylglycylamido)-6-demethyl-6-deoxytetracycline, as shown in Table I, which has good in vitro activity against tetracycline resistant strains containing the tetM resistance determinant (such as *S. aureus* UBMS 88-5, *S. aureus* UBMS 90-1 and 90-2, *E. coli* UBMS 89-1 and 90-4) and is equally as effective as minocycline against susceptible strains.

Most importantly, these compounds also exhibit antibacterial activity against bacteria that contain an active efflux resistant mechanism as in tetA, tetB, or tetK (i.e., E. coli UBMS 88-1, E. coli PRPI tetA, E. coli Me4100 TN10-tetB, and S. aureus UBMS 88-7 tetK).

As can be seen from Table I, compounds of the invention may be used to prevent or control important mammalian and veterinary diseases such as diarrhea, urinary tract infections, infections of skin and skin structure, ear, nose and throat infections, wound infections, mastitis and the like.

| | COMPOUND LEGEND FOR TABLES |
|---|---|
| A | [4S-(4α,12aα)]-8-Chloro-4-(dimethylamino)-9-[[(dimethylamino)acetyl]amino]-1,4,4a,5,5a,-6,11,12a-octahydro-3,10,12,12a-tetrahydroxy-1,11-dioxo-2-naphthacenecarboxamide disulfate. |
| B | [4S-(4α,12aα)]-8-Chloro-4,7-(dimethylamino) -9-[[(dimethylamino)acetyl]amino]-1,4,4a,5,5a,6,-11,12a-octahydro-3,10,12,12a-tetrahydroxy-1,11-dioxo-2-naphthacenecarboxamide. |
| C | [(4S-(4α,12aα)]-8-Chloro-4- (dimethylamino) -9-[[(dimethylamino)acetyl]amino)-1,4,4a,5,5a,-6,11,12a-octahydro-3,10,12,12a-tetrahydroxy-1,11-dioxo-2-naphthacenecarboxamide. |
| D | [4S-(4α,12aα)]-9-(Butylamino) acetyl ]amino]-8-chloro-4-(dimethylamino)-1,4,4a,5,5a,6,11,12a-octahydro-3,10,12,12a-tetrahydroxy-1,11-dioxo-2-naphthacenecarboxamide dihydrochloride. |
| E | [7S-(7α,10aα)]-N-[9- (Aminocarbonyl) -3-chloro-7-(dimethylamino)-5,5a,6,6a,7,10,10a,12-octahydro-1,8,10a,11-tetrahydroxy-10,12-dioxo-2-naphthacenyl]-1-pyrrolidineacetamide dihydrochloride. |
| F | [4S-(4α,12aα)]-8-Chloro-4-(dimethylamino)-1,4,-4a,5,5a,6,11,12a-octahydro-3,10,12,12a-tetrahydroxy-1,11-dioxo-9-[[(propylamino)acetyl]amino]-2-naphthacenecarboxamide dihydrochloride. |
| G | [4S-(4α,12aα)]-8-Chloro-9-(cyclopropylmethylamino)acetyl]amino]-4-(dimethylamino)-1,4,4a,5,-5a,6,11,12a-octahydro-3,10,12,12a-tetrahydroxy-1,11-dioxo-2-naphthacenecarboxamide dihydrochloride. |
| H | [4S-(4α,12aα)]-8-Chloro-4-(dimethylamino)-1,4,4a,-5,5a,6,11,12a-octahydro-3,10,12,12a-tetrahydroxy-1,11-dioxo-9-[[(pentylamino)acetyl]amino]-2-naphthacenecarboxamide dihydrochloride. |
| I | [4S-(4α,12aα)]-8-Chloro-4-(dimethylamino)-1,4,4a,-5,5a,6,11,12a-octahydro-3,10,12,12a-tetrahydroxy-1,11-dioxo-9-[[(methylamino)acetyl]amino]-2-naphthacenecarboxamide dihydrochloride. |
| J | [7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-l-piperidineacetamide dihydrochloride. |
| K | [4S-(4α,12aα)]-9-((Chloroacetyl)amino]-8-chloro-4-(dimethylamino)-1,4,4a,5,5a,6,11,12a-octahydro-3,10,12,12a-tetrahydroxy-1,11-dioxo-2-naphthacenecarboxamide hydrochloride. |
| L | Minocycline |
| M | Tetracycline |

TABLE I

ANTIBACTERIAL ACTIVITY OF 8-(SUBSTITUTED)-9-[(SUBSTITUTED GLYCYL)AMIDO]-6-DEMETHYL-6-DEOXYTETRACYCLINES MIC (ug/ml)

| Organism | Compound | | | | | | | |
|---|---|---|---|---|---|---|---|---|
| | A | B | C | D | E | F | G | H |
| E. coli UBMS 88-1 Tet V | 2 | 32 | 1 | 2 | 1 | 0.5 | 1 | 2 |
| E. coli J3272 Tet sens | 1 | NT | NT | NT | NT | NT | NT | NT |
| E. coli MC 4100 Tet sens. | NT | 2 | 0.25 | 0.25 | 0.25 | 0.12 | 0.25 | 0.25 |
| E. coli PRPI Tet A | 4 | 16 | 8 | 4 | 2 | 4 | 4 | 2 |
| F. coli MC 4100 TNIOC Tet B | 2 | 32 | 1 | 1 | 1 | 0.5 | 1 | 2 |
| E. coli J3272 Tet C | 8 | 16 | 8 | 2 | 1 | 1 | 1 | 2 |
| E. coli USMS 89-1 Tet M | 0.5 | 32 | 0.25 | 0.5 | 0.25 | 0.5 | 0.5 | 0.5 |
| E. coli UBMS 89-2 Tet sens. | 2 | 16 | 1 | 2 | 1 | 1 | 1 | 2 |
| E. coli J2175 | 1 | 32 | 1 | 1 | 1 | 1 | 1 | 2 |
| E. coli BAJ9003 IMP MUT | 0.25 | 0.12 | 0.12 | 0.25 | 0.12 | 0.12 | 0.12 | 0.25 |
| E. coli USMS 90-4 Tet M | 1 | >32 | 0.5 | 1 | 1 | 0.5 | 1 | 2 |
| E. coli UBMS 90-5 | 1 | 32 | 1 | 1 | 1 | 0.5 | 1 | 2 |
| E. coli #311 (MP) | 0.5 | 4 | 0.5 | 1 | 0.25 | 0.5 | 1 | 2 |
| E. coli ATCC 25922 | 0.5 | 8 | 0.5 | 1 | 0.25 | 0.5 | 1 | 2 |
| E. coli J3272 Tet D | 0.5 | 32 | 0.5 | 1 | 0.25 | 0.25 | 1 | 1 |
| S. mariescens FPOR 8733 | 16 | >32 | 8 | 16 | 8 | 8 | 8 | 16 |
| X. maltophilia NEMC 87210 | 2 | 0.5 | 0.05 | 4 | 1 | 2 | 4 | 4 |
| Ps. acruginosa ATCC 27853 | >32 | >32 | >32 | >32 | 32 | 32 | 32 | >32 |
| S. aureus NEMC 8769 | 0.06 | 0.12 | 0.03 | 0.5 | 0.25 | 0.25 | 0.5 | 0.5 |
| S. aureus UBMS 88-4 | 0.12 | 0.25 | 0.12 | 0.5 | 0.25 | 0.25 | 0.5 | 0.5 |
| S. aureus USMS 88-5 Tet M | 0.25 | 0.25 | 2 | 1 | 0.25 | 0.5 | 0.5 | 1 |
| S. aureus UBMS 88-7 Tet K | 2 | 2 | 0.25 | 8 | 2 | 8 | 8 | 4 |
| S. aureus URMS 90-1 Tet M | 0.5 | 0.5 | 4 | 2 | 0.25 | 0.5 | 2 | 2 |
| S. aureus UBMS 90-3 | 0.12 | 0.12 | 0.12 | 0.12 | 0.12 | 0.5 | 0.12 | 0.25 |
| S. aureus UBMS 90-2 Tet M | 0.5 | 0.25 | 1 | 0.5 | 0.25 | 0.25 | 0.5 | 0.25 |
| S. aureus IVES 2943 | 4 | 4 | 4 | 16 | 4 | 16 | 16 | 8 |
| S. aureus ROSE (MP) | 116 | 8 | 1 | 16 | 8 | 16 | 32 | 8 |
| S. aureus SMITH (MP) | 0.25 | 0.12 | 0.12 | 0.5 | 0.25 | 0.25 | 0.5 | 0.5 |
| S. aureus IVES 1 983 | 4 | 4 | 4 | 8 | 4 | 8 | 16 | 4 |
| S. aureus ATCC 29213 | 0.03 | 0.25 | 0.25 | 0.5 | 0.25 | 0.25 | 0.25 | 0.5 |
| S. hemolyticus AVHAH 88-3 | 1 | 0.5 | 0.5 | 8 | 2 | 4 | 8 | 4 |
| Enterococcus 12201 | 0.25 | 0.12 | 8 | 0.5 | 0.25 | 0.25 | 0.25 | 0.25 |
| E. faecalis ATCC 29212 | 0.12 | 0.12 | 0.5 | 0.25 | 0.12 | 0.12 | 0.25 | 0.12 |

| Organism | Compound | | | | |
|---|---|---|---|---|---|
| | I | J | K | L | M |
| E. coli UBMS 88-1 Tet V | 1 | 4 | >32 | 16 | >32 |
| E. coli J3272 Tet sens | NT | NT | NT | NT | NT |
| E. coli MC 4100 Tet sens. | 0.25 | 1 | 8 | 0.25 | 0.5 |
| E. coli PRPI Tet A | 16 | 8 | >32 | 4 | 32 |
| F. coli MC 4100 TNIOC Tet B | 1 | 4 | >32 | 8 | >32 |
| E. coli J3272 Tet C | 16 | 4 | >32 | 2 | >32 |

TABLE I-continued

ANTIBACTERIAL ACTIVITY OF 8-(SUBSTITUTED)-9-[(SUBSTITUTED GLYCYL)AMIDO]-6-DEMETHYL-6-DEOXYTETRACYCLINES MIC (ug/ml)

| | | | | | |
|---|---|---|---|---|---|
| E. coli USMS 89-1 Tet M | 2 | 1 | 8 | 16 | 32 |
| E. coli UBMS 89-2 Tet sens. | 2 | 4 | >32 | 1 | 2 |
| E. coli J2175 | 1 | 4 | >32 | 1 | 2 |
| E. coli BAJ9003 IMP MUT | 0.25 | 0.25 | 1 | 0.06 | 0.5 |
| E. coli USMS 90-4 Tet M | 1 | 4 | >32 | >32 | 32 |
| E. coli UBMS 90-5 | 1 | 4 | >32 | 1 | 1 |
| E. coli #311 (MP) | 2 | 2 | 16 | 1 | 1 |
| E. coli ATCC 25922 | 1 | 2 | 16 | 1 | 1 |
| E. coli J3272 Tet D | 1 | 2 | >32 | 8 | >32 |
| S. mariescens FPOR 8733 | 16 | >32 | >32 | 8 | >32 |
| X. maltophilia NEMC 87210 | 16 | 4 | 8 | 0.25 | 8 |
| Ps. acruginosa ATCC 27853 | 16 | >32 | >32 | 8 | 16 |
| S. aureus NEMC 8769 | 0.5 | 0.5 | 0.5 | 0.12 | 0.25 |
| S. aureus UBMS 88-4 | 0.5 | 1 | 0.5 | 0.12 | 0.25 |
| S. aureus USMS 88-5 Tet M | 0.5 | 1 | 1 | 8 | >32 |
| S. aureus UBMS 88-7 Tet K | >32 | 2 | 4 | 0.25 | >32 |
| S. aureus URMS 90-1 Tet M | 0.5 | 2 | 1 | 8 | >32 |
| S. aureus UBMS 90-3 | 0.5 | 0.25 | 0.25 | 0.06 | 0.25 |
| S. aureus UBMS 90-2 Tet M | 0.5 | 0.5 | 0.5 | 4 | 32 |
| S. aureus IVES 2943 | >32 | 2 | 4 | 4 | >32 |
| S. aureus ROSE (MP) | >32 | 4 | 4 | 1 | >32 |
| S. aureus SMITH (MP) | 0.5 | 1 | 0.5 | 0.12 | 0.25 |
| S. aureus IVES 1 983 | >32 | 4 | 4 | 4 | >32 |
| S. aureus ATCC 29213 | 0.5 | 0.5 | 0.5 | 0.12 | 0.25 |
| S. hemolyticus AVHAH 88-3 | 2 | 4 | 4 | 0.25 | 1 |
| Enterococcus 12201 | 0.5 | 0.5 | 2 | 8 | >32 |
| E. faecalis ATCC 29212 | 0.25 | 0.25 | 0.5 | 4 | 16 |

When the compounds are employed as antibacterials, they can be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing for example, for about 20 to 50% ethanol and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

An effective amount of compound from 2.0 mg/kg of body weight to 100.0 mg/kg of body weight should be administered one to five times per day via any typical route of administration including but not limited to oral, parenteral (including subcutaneous, intravenous, intramuscular, intrasternal injection or infusion techniques), topical or rectal, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserve against the contaminating action of microorganisms such as bacterial and fungi. The carrier can be a solvent or dispersion medium containing, for example, water, ethanol, polyol (e.g., glycerol, propylene glycol and liquid polyethylene glycol), suitable mixtures thereof, and vegetable oil.

The invention will be more fully described in conjunction with the following specific examples which are not be construed as limiting the scope of the invention.

EXAMPLE 1

[7S-(7alpha, 10alpha)]-9-(Aminocarbonyl)-4,7-bis(dimethylamino)-5,5a,6,6a,7,10,10a,12-octahydro-1,8,10a,11- tetrahydroxy-10,12-dioxo-2-naphthacenediazonium chloride sulfate (1:1)

To a 0° C. solution of 3.0 g of 9-amino-4,7-bis(dimethylamino)-1,4,4a,5,5a,6,11,12a-octahydro-3,10-12,12a-tetrahydroxy-1,11-dioxo-2-naphthacenecarboxamide sulfate, dissolved in 100 ml of 0.1N methanolic hydrogen chloride is added, dropwise, 6.6 ml of butyl nitrite. The reaction is stirred at 0° C. for 1 hour, poured into 400 ml of diethyl ether, collected and dried to give 2.64 g of the desired product.

MS(FAB): m/z 484 (M+H)

EXAMPLE 2

[4S-(4α, 12aα)]-9-Azido-4,7-bis(dimethylamino)-1,4,4a,5,5a,6,11,12a-octahydro-3,10,12,12a-tetrahydroxy-1,11, dioxo-2-naphthacenecarboxamide hydrochloride (1:1)

To a room temperature solution of 2.64 g of product from Example 1 dissolved in 84 ml of 0.1N methanolic hydrogen chloride is added 0.353 g of sodium azide. The mixture is stirred at room temperature for 4 hours, poured into 500 ml of diethyl ether and collected to give 2.5 g of the desired product.

IR(KBr): 2080 cm$^{-1}$.

EXAMPLE 3

9-Amino-8-chloro-4,7-bis(dimethylamino)-1,4,4a,5,5a,6,11,12a-octahydro-3,10,12,12a-tetrahydroxy-1,11-dioxo-2 naphthacenecarboxamide sulfate One gram of product from Example 2 is added to 10 ml of 0° C. concentrated sulfuric acid. The reaction is stirred at 0° C. for 1.5 hours, poured into 500 ml of diethyl ether, collected and dried to give 1.1 g of the desired product.

MS(FAB): m/z 507 (M+H).

EXAMPLE 4

[4S-(4α, 12aα)]-9-Amino-4,7-bis(dimethylamino)-8-fluoro-1,4,4a,5,5a,6,11,12a-octahydro-3,10,12,12a-tetrahydroxy-1,11-dioxo-2-naphthacenecarboxamide The title compound is prepared by the procedure of Example 3 using the product of Example 2 and liquid hydrogen fluoride.

EXAMPLE 5

9-Amino-8-chloro-4-(dimethylamino)-1,4,4a,5,5a,6,11,-12a-octahydro-3,10,12,12a-tetrahydroxy-1,11-dioxo-2-naphthacenecarboxamide hydrochloride (1:1)

To 10 ml of concentrated hydrochloric acid at 0° C. is added 0.20 g of 9-azido-6-demethyl-6-deoxytetracycline hydrochloride prepared by the procedure described in J. Am. Chem. Soc., 84: 1426–1430. The reaction is stirred at 0° C. for 1½ hours and concentrated in vacuo to give 0.195 g of the desired product.

MS(FAB): m/z 464 (M+H).

EXAMPLE 6

[4S-(4α,12aα)]-9-Amino-4-(dimethylamino)-8-fluoro-1,4,4a,5,5a,6,11,12a-octahydro-3,10,12,12a-tetrahydroxy-1,11-dioxo-2-naphthacene carboxamide The title compound is prepared by the procedure of Example 3 using 9-azido-6-demethyl-6-deoxytetracycline and liquid hydrogen fluoride.

EXAMPLE 7

[4S-(4α,12aα)]-9-Amino-4,7-bis(dimethylamino)-1,4,4a,5,5a,6,11,12a-octahydro-3,10,12,12a-tetrahydroxy-1,11-dioxo-8-[[(trifluoromethyl)sulfonyl]oxy]-2-naphthacenecarboxamide The title compound is prepared by the procedure of Example 3 using 9-azido-4,7-bis(dimethylamino)-6-demethyl-6-deoxytetracycline and trifluoromethanesulfonic acid.

EXAMPLE 8

[4S-(4α,12aα)]-9-Amino-4-(dimethylamino)-1,4,4a,5,5a,6,11,12a-octahydro-3,10,12,12a,tetrahydroxy-1,11-dioxo-8-[[(trifluoromethyl)sulfonyl]oxy]-2-naphthacenecarboxamide The title compound is prepared by the procedure of Example 3 using 9-azido-4-(dimethylamino)-6-demethyl-6-deoxytetracycline and trifluoromethanesulfonic acid.

EXAMPLE 9

[4S-(4α,12aα)]-9-[(Chloroacetyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide.

A well-stirred cold solution of 1.0 g of product from Example 3, 2 ml of 1,3-dimethyl-2-imidazolidinone and 1.0 g of sodium bicarbonate is treated with 0.30 ml of chloroacetyl chloride. The solution is stirred at 25° C. for 30 minutes, filtered and the filtrate added dropwise to 500 ml of diethyl ether to afford 1.0 g of yellow product.

EXAMPLE 10

[4S-(4α,12aα)]-9-[(Bromoacetyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide.

A well-stirred cold solution of 1.0 g of product from Example 3, 2 ml of 1,3-dimethyl-2-imidazolidinone and 1.0 g of sodium bicarbonate was treated with 0.36 ml of bromoacetyl bromide. The solution was stirred at 25° C. for 30 minutes, filtered and the filtrate added dropwise to 500 ml of diethyl ether to afford 0.7 g of yellow product.

EXAMPLE 11

[4S-(4α,12aα)]-9-[(α-Bromopropionyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide.

A well-stirred cold solution of 1.0 g of product from Example 3, 2 ml of 1,3-dimethyl-2-imidazolidinone and 1.0 g of sodium bicarbonate was treated with 0.42 ml of bromopropionyl bromide. The solution was stirred at 25° C. for 30 minutes, filtered and the filtrate added dropwise to 500 ml of diethyl ether to afford 1.0 g of yellow product.

Substantially following the method, described in detail herein above in Example 10, the compounds of the invention listed in Examples 12–19 are prepared.

EXAMPLE 12

[4S-(4α,12aα)]-9-[(α-Bromocyclobutylacetyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide

EXAMPLE 13

[4S-(4α,12aα)]-9-[(α-Bromophenylacetyl)amino]-8-chloro-4,7-bis(dimethylamino)-1,4,4a,5,5a,6,11,12a- octahydro-3,10,12,12a-tetrahydroxy-1,11-dioxo-2-naphthacenecarboxamide

EXAMPLE 14

[4S-(4α,12aα)]-9-[(α-Bromo-α-cyclopropylpropionyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide

EXAMPLE 15

[4S-(4α,12aα)]-9-[(α-Bromo-2,2-dimethylbutyryl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide

EXAMPLE 16

[4S-(4α,12aα)]-9-[(α-Bromo-(2,4-difluorophenyl)acetyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide

EXAMPLE 17

[4S-(4α,12aα)]-9-[(α-Bromo-(2-furyl)propionyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide

EXAMPLE 18

[4S-(4α,12aα)]-9-[(α-Bromo-(3-methoxycarbonylpropionyl))amino]-8-chloro-4,7-bis(dimethylamino)-1,4,4a,5,5a,6,11,12a-octahydro-3,10,12,12a-tetrahydroxy-1,11-dioxo-2-naphthacenecarboxamide

EXAMPLE 19

[4S-(4α,12aα)]-9-[(α-Bromo-(4-methoxycarbonylbutyryl))amino]-8-chloro-4,7-bis(dimethylamino)-1,4,4a,5,5a,6,11,12a-octahydro-3,10,12,12a-tetrahydroxy-1,11-dioxo-2-naphthacenecarboxamide

EXAMPLE 20

[4S-(4α,12aα)]-9[(Bromoacetyl)amino]-4,7-bis(dimethylamino)-8-fluoro-1,4,4a,5,5a,6,11,12a-octahydro-3,10,12,12a-tetrahydroxy-1,11-dioxo-2-naphthacenecarboxamide The title compound is prepared by the procedure of Example 10 using the product from Example 4.

EXAMPLE 21

[4S-(4α,12aα)]-9-(Bromoacetyl)amino]-4,7-bis(dimethylamino)-1,4,4a,5,5a,6,11,12a-octahydro-3,10,12,12a-tetrahydroxy-1,11-dioxo-8-[[(trifluoromethyl)sulfonyl]oxy]-2-naphthacenecarboxamide The title compound is prepared by the procedure of Example 10 and using the product from Example 7.

EXAMPLE 22

[4S-(4α,12aα)]-9-[(Chloroacetyl)amino]-8-chloro-4-(dimethylamino)-1,4,4a,5,5a,6,11,12a-octahydro-3,10,12,12a-tetrahydroxy-1,11-dioxo-2-naphthacenecarboxamide hydrochloride A 25° C. solution of 1.247 g of product from Example 5, 12 ml of DMPU and 6 ml of acetonitrile is treated with 0.564 g of chloroacetyl chloride. The mixture is stirred for 45 minutes and added dropwise to a mixture of 80 ml of 2-propanol and 400 ml of diethyl ether. The resultant yellow solid is filtered and washed several times with diethyl ether and dried in vacuo to give 1.25 g of product.

MS (FAB)=m/z 540 (M+H)

EXAMPLE 23

[4S-(4α,12aα)]-9-[(Bromoacetyl)amino]-8-chloro-4-(dimethylamino)-1,4,4a,5,5a,6,11,12a-octahydro-3,10,12,12a-tetrahydroxy-1,11-dioxo-2-naphthacenecarboxamide hydrobromide A 25° C. solution of 1.247 g of product from Example 5, 12 ml of DMPU and 6 ml of acetonitrile is treated with 0.62 g of bromoacetyl bromide. The mixture is stirred for 45 minutes and added dropwise to a mixture of 80 ml of 2-propanol and 400 ml of diethyl ether. The resultant yellow solid is filtered and washed several times with diethyl ether and dried in vacuo to give 1.35 g of product.

Substantially following the method, described in detail herein above in Example 22 or 23, the compounds of the invention listed in Examples 24–30 are prepared.

EXAMPLE 24

[4S-(4α,12aα)]-9-[(Chloropropionyl)amino]-8-chloro-4-(dimethylamino)-1,4,4a,5,5a,6,11,12a-octahydro-10,12,12a-tetrahydroxy-1,11-dioxo-2-naphthacenecarboxamide hydrochloride

EXAMPLE 25

[4S-(4α,12aα)]-9-[(Chlorobutyryl)amino]-8-chloro-4-(dimethylamino)-1,4,4a,5,5a,6,11,12a-octahydro-3,10,12,12a-tetrahydroxy-1,11-dioxo-2-naphthacenecarboxamide hydrochloride

EXAMPLE 26

[4S-(4α,12aα)]-9-[[(4-Hydroxyphenyl)-α-chloroacetyl]amino]-8-chloro-4-(dimethylamino)-1,4,4a,5,5a,6,11,12a-octahydro-3,10,12,12a-tetrahydroxy-1,11-dioxo-2-naphthacenecarboxamide hydrochloride

EXAMPLE 27

[4S-(4α,12aα)]-9-[[(2-Fluorophenyl)-α-bromoacetyl]amino]-8-chloro-4-(dimethylamino)-1,4,4a,5,5a,6,11,12a-octahydro-3,10,12,12a-tetrahydroxy-1,11-dioxo-2-naphthacenecarboxamide hydrobromide

EXAMPLE 28

[4S-(4α,12aα)]-9-[(2-Bromo-4-pentenoyl)amino]-8-chloro-4-(dimethylamino)-1,4,4a,5,5a,6,11,12a-octahydro-3,10,12,12a-tetrahydroxy-1,11-dioxo-2-naphthacenecarboxamide hydrobromide

EXAMPLE 29

[4S-(4α,12aα)]-9-[(α-Bromophenylbutyryl)amino]-8-chloro-4-(dimethylamino)-1,4,4a,5,5a,6,11,12a-octahydro-3,10,12,12a-tetrahydroxy-1,11-dioxo-2-naphthacenecarboxamide hydrobromide

EXAMPLE 30

[4S-(4α,12aα)]-9-[((4-Pyridyl)-α-bromoacetyl)amino]-8-chloro-4-(dimethylamino)-1,4,4a,5,5a,6,11,12a-octahydro-3,10,12,12a-tetrahydroxy-1,11-dioxo-2-naphthacenecarboxamide hydrobromide

EXAMPLE 31

[4S-(4α,12aα)]-9-[(Bromoacetyl)amino]-4-(dimethylamino)-8-fluoro-1,4,4a,5,5a,6,11,12a-octahydro-3,10,12,12a-tetrahydroxy-1,11-dioxo-2-naphthacenecarboxamide The title compound is prepared by the procedure of Example 10 using the product from example 6.

EXAMPLE 32

[4S-(4α,12aα)]-9-[(Bromoacetyl)amino]-4-(dimethylamino)-1,4,4a,5,5a,6,11,12a-octahydro-3,10,12,12a-tetrahydroxy-1,11-dioxo-8-[[(trifluoromethyl)sulfonyl]oxy]-2-naphthacenecarboxamide The title compound is prepared by the procedure of Example 10 using the product from Example 8.

EXAMPLE 33

[4S-(4α,12aα)]-8-Chloro-4-(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide disulfate A well stirred solution (25° C.) of 0.2805 g of product from Example 5, 10 ml of DMPU, 3 ml of acetonitrile and 0.3 g of sodium carbonate is treated with 0.157 g of N,N-dimethylaminoacetyl chloride hydrochloride. After 30 minutes, the reaction is filtered and the filtrate is added dropwise to 300 ml of diethyl ether. Concentrated sulfuric acid is added dropwise and a yellow solid precipitated. The yellow solid is collected, washed well with ether, and dried in vacuo to afford 0.21 g of product:

MS (FAB)=m/z 549 (M+H).

EXAMPLE 34

[4S-(4α,12aα)]-8-Chloro-4-(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide A well stirred solution 25° C. of 0.20 g of product from Example 5, 3 ml of N-methylpyrrolidone, 1 ml of acetonitrile and 0.2 g of sodium bicarbonate is treated with 0.071 g of N,N-dimethylaminoacetyl chloride hydrochloride. After 30 minutes, the reaction is filtered and the filtrate is added dropwise to 200 ml of diethyl ether. The yellow solid is collected, washed well with ether, and dried in vacuo to afford 0.15 g of product:

MS (FAB)=m/z 548 (M+H).

EXAMPLE 35

[4S-(4α,12aα)]-8-Chloro-4,7-(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide A well stirred solution (25° C.) of 0.104 g of product from Example 3, 1.5 ml of N-methylpyrrolidone, 0.5 ml of acetonitrile and 0.105 g of sodium bicarbonate is treated with 0.034 g of N,N-dimethylaminoacetyl chloride hydrochloride. After 1 hr, the reaction is filtered and the filtrate is added dropwise to 100 ml of diethyl ether. The yellow solid is collected, washed well with ether, and dried in vacuo to afford 0.085 g of product:

MS (FAB)=m/z 591 (M+H).

EXAMPLE 36

[4S-(4α,12aα)]-9-[[(Butylamino)acetyl]amino]-8-chloro-4,7-bis(dimethylamino)-1,4,4a,5,5a,6,11,12a-octahydro-3,10,12,12a-tetrahydroxy-1,11-dioxo-2-naphthacenecarboxamide A solution of 0.20 g of the product from Example 10, 2 ml of 1,3-dimethyl-2-imidazolidinone and 0.1 ml of n-butylamine is stirred at room temperature for 1 hr and added dropwise to 50 ml of diethyl ether to afford 0.20 g of yellow color product:

MS (FAB) m/z 620 (M+H).

Substantially following the method, described in detail herein above in Example 36, the compounds of the invention listed in Examples 37–45 are prepared.

EXAMPLE 37

[4S-(4α,12aα)]-8-Chloro-4,7-bis(dimethylamino)-1,4,4a,5,5a,6,11,12a-octahydro-3,10,12,12a-tetrahydroxy-9-[[[(3-methylcyclobutyl)amino]acetyl]amino]-1,11-dioxo-2-naphthacenecarboxamide

EXAMPLE 38

[7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-1H-pyrrole-1-acetamide

EXAMPLE 39

[7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-1H-pyrazole-1-acetamide

EXAMPLE 40

[4S-(4a, 12aα)]-8-Chloro-4,7-bis(dimethylamino)-9-[[[(1,1-dimethylethyl)amino]acetyl]amino]-1,4,4a,5,5a,6,11,12a-octahydro-3,10,12,12a-tetrahydroxy-1,11-dioxo-2-naphthacenecarboxamide

EXAMPLE 41

[4S-(4α,12aα)]-8-Chloro-9-[[(cyclopropylamino)acetyl]amino]-4,7-bis(dimethylamino)-1,4,4a,5,5a,6,11,12a-octahydro-3,10,12,12a-tetrahydroxy-1,11-dioxo-2-naphthacenecarboxamide

EXAMPLE 42

[4S-(4α,12aα)]-8-Chloro-9-[[[(cyclobutyloxy)amino]acetyl]amino]-4,7-bis(dimethylamino)-1,4,4a,5,5a,6,11,12a-octahydro-3,10,12,12a-tetrahydroxy-1,11-dioxo-2-naphthacenecarboxamide

EXAMPLE 43

[7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-1-pyrrolidineacetamide

EXAMPLE 44

[7S-(7α,10aα)]-N-[9-(Aminocarbonyl)-3-chloro-4,7-bis(dimethylamino)-5,5a,6,6a,7,10,10a,12-octahydro-1,8,9,10a,11-tetrahydroxy-10,12-dioxo-2-naphthacenyl]-(3-methyl-1-pyrrolidine)acetamide

EXAMPLE 45

[4S-(4α,12aα)]-8-Chloro-4,7-bis(dimethylamino)-1,4,4a,5,5a,6,11,12a-octahydro-3,10,12,12a-tetrahydroxy-1,11-dioxo-9-[[[(propylamino)]acetyl]amino]-2-naphthacenecarboxamide

EXAMPLE 46

[4S-(4α,12aα)]-8-Chloro-4,7-bis(dimethylamino)-1,4,4a,5,5a,6,11,12a-octahydro-3,10,12,12a-tetrahydroxy-1,11-dioxo-9-[[1-oxo-2-(propylamino)propyl]amino]-2-naphthacenecarboxamide The title compound is prepared by the procedure of Example 36 using [4S-(4α,12aα)]-9-[(α-bromopropionyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide and n-propylamine.

EXAMPLE 47

[7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-α-cyclobutyltetrahydro-2H-1,2-isoxazine-2-acetamide The title compound is prepared by the procedure of Example 36 using [4S-(4α,12aα)]-9-[(α-bromocyclobutylacetyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide and tetrahydro-1,2-oxazine.

EXAMPLE 48

[4S-(4α,12aα)]-8-Chloro-4,7-bis(dimethylamino)-1,4,4a,5,5a,6,11,12a-octahydro-3,10,12,12a-tetrahydroxy-1,11-dioxo-9-[[phenyl[(phenylmethyl)amino]acetyl]amino]-2-naphthacenecarboxamide The title compound is prepared by the procedure of Example 36 using [4S-(4α,12aα)]-9-[(α-bromophenylacetyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide and benzylamine.

EXAMPLE 49

[7S-(7α,10aα)]-N-[9-(Aminocarbonyl)-3-chloro-4,7--bis(dimethylamino)-5,5a,6,6a,7,10,10a,12-octahydro-1,8,10a,11-tetrahydroxy-10,12-dioxo-2-naphthacenyl]-α-cyclopropyl-α-methyl-1-azetidineacetamide The title compound is prepared by the procedure of Example 36 using [4S-(4α,12aα)]-9-[(α-bromo-α-cyclopropylpropionyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide and azetidine.

EXAMPLE 50

[7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-α-(1,1-dimethylethyl)-(3-methyl-4-morpholine)acetamide The title compound is prepared by the procedure of Example 36 using [4S-(4α,12aα)]-9-](α-bromo-2,2-dimethylbutyryl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide and 3-methyl-4-morpholine.

EXAMPLE 51

[4S-(4α,12aα)]-8-Chloro-9-[[(2,4-difluorophenyl)[(2-phenylethyl)amino]acetyl]amino]-4,7-bis(dimethylamino)-1,4,4a,5,5a,6,11,12a-octahydro-3,10,12,12a-tetrahydroxy-1,11-dioxo-2-naphthacenecarboxamide The title compound is prepared by the procedure Example 36 using [4S-(4α,12aα)]-9-[(α-bromo-(2,4-difluorophenyl)acetyl)amino]-8-chloro-4,7-bis(dimethylamino)-1,4,4a,5,5a,6,11,12a-octahydro-3,10,12,12a-tetrahydroxy-1,11-dioxo-2-naphthacenecarboxamide and 2-phenethylamine.

EXAMPLE 52

[7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-α-(methoxyamino)-α-methyl-2-furanacetamide The title compound is prepared by the procedure of Example 36 using [4S-(4α,12aα)]-9-[(α-bromo-(2-furyl)-propionyl))amino]-8-chloro-4,7-bis(dimethylamino)-1,4,4a,5,5a,6,11,12a-octahydro-3,10,12,12a-tetrahydroxy-1,11-dioxo-2-naphthacenecarboxamide and methoxyamine.

Substantially following the method, described in detail herein above in Example 36, the compounds of the invention listed in Examples 53–54 are prepared from [4S-(4α,12aα)]-9-[(α-bromo-(3-methoxycarbonylpropionyl))amino]-8-chloro-4,7-bis(dimethylamino)-1,4,4a,5,5a,6,11,12a-octahydro-3,10,12,12a-tetrahydroxy-1,11-dioxo-2-naphthacenecarboxamide.

EXAMPLE 53

[7S-(7α,10aα)]-4-[[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]amino-3-[(1,1-dimethylethyl)amino]-4-oxobutanoic acid methyl ester

EXAMPLE 54

[7S-(7α,10aα)]-4-[[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]amino]-3-(dimethylamino)-4-oxobutanoic acid methyl ester

EXAMPLE 55

[7S-(7α,10aα)]-γ-[[[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl-]amino]carbonyl]-1-pyrrolidinebutanoic acid methyl ester The title compound is prepared by the procedure of Example 36 using [4S-(4α,12aα)]-9-[(α-bromo-(4-methoxycarbonylbutyryl))amino]-8-chloro-4,7-bis(-dimethylamino)-1,4,4a,5,5a,6,11,12a-octahydro-3,10,12,12a-tetrahydroxy-1,11-dioxo-2-naphthacenecarboxamide and pyrrolidine.

EXAMPLE 56

[4S-(4α,12aα)]-4,7-Bis(Dimethylamino)-9-[[(dimethylamino)acetyl]amino]-8-fluoro-1,4,4a,5,5a,6,11,12a-octahydro-3,10,12,12a-tetrahydroxy-1,11-dioxo-2-naphthacenecarboxamide The title compound is prepared by the procedure of Example 36 using [4S-(4α,12aα)]-9-[(bromoacetyl)amino]-4,7-bis(dimethylamino)-8-fluoro-1,4,4a,5,,5a,6,11,12a-octahydro-3,10,12,12a-tetrahydroxy-1,11-dioxo-2-naphthacenecarboxamide and dimethylamine.

EXAMPLE 57

[4S-(4α,12aα)]-9-[[(Butylamino)acetyl]amino]-8-chloro-4-(dimethylamino)-1,4,4a,5,5a,6,11,12a-octahydro-3,10,12,12a-tetrahydroxy-1,11-dioxo-2-naphthacenecarboxamide dihydrochloride A mixture of 0.20 g of the product from Example 22, 0.5 g of n-butylamine and 3 ml of DMPU, under argon, is stirred at room temperature for 2 h. The excess n-butylamine was removed in vacuo and the solids filtered. The filtrate is diluted with a small amount of methanol and the solution added dropwise to a mixture of 10 ml of 2-propanol and 120 ml of diethyl ether. The solution is treated dropwise with 1.0M hydrogen chloride-diethyl ether solution to afford a yellow solid. The resulting solid is collected and dried in vacuo to afford 0.175 g of product:

MS (FAB)=m/z 576 (M+H)

Substantially following the method described in detail herein above in Example 57, the compounds of the invention listed below in Examples 58–66 are prepared.

EXAMPLE 58

[4S-(4α,12aα)]-8-Chloro-4-(dimethylamino)-1,4,4a,5,5a,6,11,12a-octahydro-3,10,12,12a-tetrahydroxy-1,11-dioxo-9-[[(propylamino)acetyl]amino]-2-naphthacenecarboxamide dihydrochloride

EXAMPLE 59

[4S-(4α,12aα)]-8-Chloro-4-(dimethylamino)-1,4,4a,5,5a,6,11,12a-octahydro-3,10,12,12a-tetrahydroxy-1,11-dioxo-9-[[(pentylamino)acetyl]amino]-2-naphthacenecarboxamide dihydrochloride

EXAMPLE 60

[4S-(4α,12aα)]-8-Chloro-4-(dimethylamino)-1,4,4a,5,5a,6,11,12a-octahydro-3,10,12,12a-tetrahydroxy-1,11-dioxo-9-[[(methylamino)acetyl]amino]-2-naphthacenecarboxamide dihydrochloride

EXAMPLE 61

[4S-(4α,12aα)]-8-Chloro-9-[[(cyclopropylmethylamino)acetyl]amino]-4-(dimethylamino)-1,4,4a,5,5a,6,11,12a-octahydro-3,10,12,12a-tetrahydroxy-1,11-dioxo-2-naphthacenecarboxamide dihydrochloride

EXAMPLE 62

[7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-1-pyrrolidineacetamide dihydrochloride

EXAMPLE 63

[7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-1-piperidineacetamide dihydrochloride

EXAMPLE 64

7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-5-azabicyclo[2.1.1]hexane-5-acetamide dihydrochloride

EXAMPLE 65

[4S-(4α,12aα)]-8-Chloro-9-[[(cyclobutylamino)acetyl]amino]-4-(dimethylamino)-1,4,4a,5,5a,6,11,12a-octahydro-3,10,12,12a-tetrahydroxy-1,11-dioxo-2-naphthacenecarboxamide dihydrochloride

EXAMPLE 66

[7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-α-ethyl-1H-imidazole-1-acetamide dihydrochloride Substantially following the method, described in detail herein above in Example 36, the compounds of the invention listed in Examples 67–68 are prepared from [4S-(4α,12aα)]-9-[(bromopropionyl)amino]-8-chloro-4-(dimethylamino)-1,4,4a,5,5a,6,11,12a-octahydro-3,10,12,12a-tetrahydroxy-1,11-dioxo-2-naphthacenecarboxamide.

EXAMPLE 67

[4S-(4α,12aα)]-8-Chloro-9-[[2-(diethylamino)-1-oxopropyl]-4-(dimethylamino)-1,4,4a,5,5a,6,11,12a-octahydro-3,10,12,12a-tetrahydroxy-1,11-dioxo-2-naphthacenecarboxamide

EXAMPLE 68

[7S-(7α,10aα)]-1-[2-[[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]amino]-1-methyl-2-oxoethyl] proline methyl ester

EXAMPLE 69

[7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-α-(4-hydroxyphenyl)-6-methyl-2,6-diazabicyclo[2.1.1]heptane-2-acetamide The title compound is prepared by the procedure of Example 36 using [4S-(4α,12aα)]-9-[[(4-Hydroxyphenyl)-α-bromoacetyl]amino]-8-chloro-4-(dimethylamino)-1,4,4a,5,5a,6,11,12a-octahydro-3,10,12,12a-tetrahydroxy-1,11-dioxo-2-naphthacenecarboxamide and 6-methyl-2,6-diazabicyclo[2.1.1]heptane.

EXAMPLE 70

[4S-(4α,12aα)]-8-Chloro-4-(dimethylamino)-9-[[(dimethylamino)(2-fluorophenyl)acetyl]amino]-1,4,4a,5,5a,6,11,12a-octahydro-3,10,12,12a-tetrahydroxy-1,11-dioxo-2-naphthacenecarboxamide The title compound is prepared by the procedure of Example 36 using [4S-(4α,12aα)]-9-[[(2-fluorophenyl)-α-bromoacetyl]amino]-8-chloro-4-(dimethylamino)-1,4,4a,5,5a,6,11,12a-octahydro-3,10,12,12a-tetrahydroxy-1,11-dioxo-2-naphthacenecarboxamide and dimethylamine.

EXAMPLE 71

[4S-(4α,12aα)]-8-Chloro-4-(dimethylamino)-1,4,4a,5,5a,6,11,12a-octahydro-3,10,12,12a-tetrahydroxy-9-[[1-(4-methoxy-1-piperazinyl)-4-pentenoyl]amino]-1,11-dioxo-2-naphthacenecarboxamide The title compound is prepared by the procedure of Example 36 using [4S-(4α,12aα)]-9-[(2-bromo-4-pentenoyl)amino]-8-chloro-4-(dimethylamino)-1,4,4a,5,5a,6,11,12a-octahydro-3,10,12,12a-tetrahydroxy-1,11-dioxo-2-naphthacenecarboxamide and 4-methoxypiperazine.

EXAMPLE 72

[4S-(4α,12aα)]-8-Chloro-4-(dimethylamino)-1,4,4a,5,5a,6,11,12a-octahydro-3,10,12,12a-tetrahydroxy-1,11-dioxo-9-[[1-oxo-4-phenyl-2-[(phenylmethoxy)amino]butyl]amino]-2-naphthacenecarboxamide.

The title compound is prepared by the procedure of Example 36 using [4S-(4α,12aα)]-9-[(α-bromophenylbutyryl)amino]-8-chloro-4-(dimethylamino)-1,4,4a,5,5a,6,11,12a-octahydro-3,10,12,12a-tetrahydroxy-1,11-dioxo-2-naphthacenecarboxamide and benzyloxyamine.

EXAMPLE 73

[7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-α-4-pyridyl-5-azabicyclo[2.1.1]hexan-5-acetamide The title compound is prepared by the procedure of Example 36 using [4S-(4α,12aα)]-9-[[(4-pyridyl)-α- bromoacetyl]amino]-8-chloro-4-(dimethylamino)-1,4,4a,5,5a,6,11,12a-octahydro-3,10,12,12a-tetrahydroxy-1,11-dioxo-2-naphthacenecarboxamide and 5-azabicyclo[2.1.1]hexane.

Substantially following the method, described in detail herein above in Example 36, the compounds of the invention listed in Examples 74–75 are prepared from [4S-(4α,12aα)]-9-[(bromoacetyl)amino]-4-(dimethylamino)-8-fluoro-1,4,4a,5,5a,6,11,12a-octahydro-3,10,12,12a-tetrahydroxy-1,11-dioxo-2-naphthacenecarboxamide.

EXAMPLE 74

[4S-(4α,12aα)]-4-(Dimethylamino)-9-[[(dimethylamino)acetyl]amino]-8-fluoro-1,4,4a,5,5a,6,11,12a-octahydro-3,10,12,12a-tetrahydroxy-1,11-dioxo-2-naphthacenecarboxamide

EXAMPLE 75

[4S-(4α,12aα)]-4-(Dimethylamino)-8-fluoro-1,4,4a,5,5a,6,11,12a-octahydro-3,10,12,12a-tetrahydroxy-1,11-dioxo-9-[[(propylamino)acetyl]amino]-2-naphthacenecarboxamide.

EXAMPLE 76

[4S-(4α,12aα)]-4-(Dimethylamino)-9-[[(dimethylamino)acetyl]amino]-1,4,4a,5,5a,6,11,12a-octahydro-3,10,12,12a-tetrahydroxy-1,11-dioxo-8-[[(trifluoromethyl)sulfonyl]oxy]-2-naphthacenecarboxamide The title compound is prepared by the procedure of Example 36 using [4S-(4α,12aα)]-9-[(bromoacetyl)amino]-4-(dimethylamino)-1,4,4a,5,5a,6,11,12a-octahydro-3,10,12,12a-tetrahydroxy-1,11-dioxo-8-[[(trifluoromethyl)sulfonyl]oxy]-2-naphthacenecarboxamide and dimethylamine.

| MASS SPECTRAL DATA | |
|---|---|
| Example # | MS(FAB):m/z |
| 59 | 592 (M + H) |
| 60 | 535 (M + H) |
| 61 | 575 (M + H) |
| 63 | 589 (M + H) |

We claim:
1. A compound of the formula:

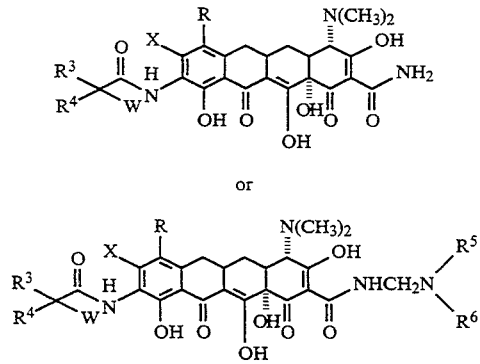

wherein:
X is halogen or trifluoromethanesulfonyloxy, the halogen is selected from bromine, chlorine, fluorine, and iodine;
R is selected from hydrogen; halogen selected from bromine, chlorine, fluorine and iodine; or R=—NR$^1$R$^2$ and R$^1$ is selected from hydrogen, methyl, ethyl, n-propyl, 1-methylethyl, n-butyl or 1-methylpropyl and R$^2$ is selected from methyl, ethyl, n-propyl, 1-methylethyl, n-butyl, 1-methylpropyl, 2-methylpropyl, or 1,1-dimethylethyl with the proviso that when R$^1$=hydrogen, R$^2$=methyl, ethyl, n-propyl, 1-methylethyl, n-butyl, 1-methylpropyl, 2-methylpropyl or 1,1-dimethylethyl;

and when R$^1$=methyl or ethyl, R$^2$=methyl, ethyl, n-propyl, 1-methylethyl, n-butyl, 1-methylpropyl or 2-methylpropyl;

and when R$^1$=n-propyl, R$^2$=n-propyl, 1-methylethyl, n-butyl, 1-methylpropyl or 2-methylpropyl;

and when R$^1$=1-methylethyl, R$^2$=n-butyl, 1-methylpropyl or 2-methylpropyl;

and when R$^1$=n-butyl, R$^2$=n-butyl, 1-methylpropyl or 2-methylpropyl;

and when R$^1$=1-methylpropyl, R$^2$=2-methylpropyl;

R$^3$ is selected from hydrogen; straight or branched (C$_1$–C$_8$)alkyl group selected from methyl, ethyl, propyl, isopropyl, butyl, isobutyl, pentyl, hexyl, heptyl and octyl; α-mercapto(C$_1$–C$_4$)alkyl group selected from mercaptomethyl, α-mercaptoethyl, α-mercapto-1-methylethyl, α-mercaptopropyl and α-mercaptobutyl; α-hydroxy-(C$_1$–C$_4$)alkyl group selected from hydroxymethyl, α-hydroxyethyl, α-hydroxy-1-methylethyl, α-hydroxypropyl and α-hydroxybutyl; carboxyl(C$_1$–C$_8$)alkyl group; (C$_6$–C$_{10}$)aryl group selected from phenyl, α-naphthyl and β-naphthyl; substituted (C$_6$–C$_{10}$)aryl group with substitution selected from hydroxy, halogen, (C$_1$–C$_4$)alkoxy, trihalo(C$_1$–C$_3$)alkyl, nitro, amino, cyano, (C$_1$–C$_4$)alkoxycarbonyl, (C$_1$–C$_3$)alkylamino and carboxy; (C$_7$–C$_9$)-aralkyl group selected from benzyl, 1-phenylethyl, 2-phenylethyl and phenylpropyl; substituted (C$_7$–C$_9$)aralkyl group with substitution selected from halo, (C$_1$–C$_4$)alkyl, nitro, hydroxy, amino, mono- or disubstituted (C$_1$–C$_4$)alkylamino, (C$_1$–C$_4$)alkoxy, (C$_1$–C$_4$)alkylsulfonyl, cyano and carboxy;

R$^4$ is selected from hydrogen and (C$_1$–C$_6$)alkyl selected from methyl, ethyl, propyl, isopropyl, butyl, isobutyl, pentyl and hexyl;

when R$^3$ does not equal R$^4$ the stereochemistry of the carbon bearing the W substituent maybe be either the racemate (DL) or the individual enantiomers (L or D);

W is selected from amino; hydroxylamino; (C$_1$–C$_{12}$) straight or branched alkyl monosubstituted amino group with substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl, heptyl, octyl, nonyl, decyl, undecyl and dodecyl and the diastereomers and enantiomers of said branched alkyl mono-substituted amino group; (C$_3$–C$_8$)cycloalkyl monosubstituted amino group with substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, bicyclo[2.2.1]hept-2-yl, and bicyclo[2.2.2]oct-2-yl and the diastereomers and enantiomers of said (C$_3$–C$_8$)cycloalkyl monosubstituted amino; [(C$_4$–C$_{10}$)cycloalkyl]alkyl monosubstituted amino group with substitution selected from (cyclopropyl)methyl, (cyclopropyl)ethyl, (cyclobutyl)methyl, (trans-2-methylcyclopropyl)methyl, and (cis-2-methylcyclobutyl)methyl; ($C_3$–$C_{10}$)alkenyl monosubstituted amino group with substitution selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; ($C_6$–$C_{10}$)aryl monosubstituted amino group with substitution selected from phenyl and naphthyl; ($C_7$–$C_{10}$)aralkylamino group selected from benzylamino, 2-phenylethylamino, 1-phenylethylamino, 2-(naphthyl)methylamino, 1-(naphthyl)methylamino and phenylpropylamino; substituted ($C_6$–$C_{10}$)aryl monosubstituted amino group with substitution for the ($C_6$–$C_{10}$) aryl group selected from ($C_1$–$C_5$)acyl, ($C_1$–$C_5$)acylamino, ($C_1$–$C_4$)alkyl, mono or disubstituted ($C_1$–$C_8$)alkylamino, ($C_1$–$C_4$)alkoxy, ($C_1$–$C_4$)alkoxycarbonyl, ($C_1$–$C_4$)alkylsulfonyl, amino, carboxy, cyano, halogen, hydroxy, nitro and trihalo($C_1$–$C_3$)alkyl; straight or branched symmetrical disubstituted ($C_2$–$C_{14}$)alkylamino group with substitution selected from dimethyl, diethyl, diisopropyl, di-n-propyl, dibutyl and diisobutyl; symmetrical disubstituted ($C_3$–$C_{14}$)cycloalkylamino group with substitution selected from dicyclopropyl, dicyclobutyl, dicyclopentyl, dicylohexyl and dicycloheptyl; straight or branched unsymmetrical disubstituted ($C_3$–$C_{14}$)alkylamino group wherein the total number of carbons in the substitution is not more than 14; unsymmetrical disubstituted ($C_4$–$C_{14}$)cycloalkylamino group wherein the total number of carbons in the substitution is not more than 14; ($C_2$–$C_8$)azacyclo- alkyl and substituted ($C_2$–$C_8$)azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept7-yl, 2-azabicyclo[2.2.2]oct-2-yl and the diastereomers and enantiomers of said ($C_2$–$C_8$)azacycloalkyl and substituted ($C_2$–$C_8$)azacycloalkyl group; 1-azaoxacycloalkyl selected from morpholinyl and 1-aza-5-oxocycloheptane; substituted 1-azaoxacycloalkyl group selected from 2-($C_1$–$C_3$)alkylmorpholinyl, 3-($C_1$–$C_3$)alkylisoxazolidinyl, tetrahydrooxazinyl and 3,4-dihydrooxazinyl; [1,n]-diazacycloalkyl and substituted [1,n]-diazacycloalkyl group selected from piperazinyl, 2-($C_1$–$C_3$)alkylpiperazinyl, 4-($C_1$–$C_3$)alkylpiperazinyl, 2,4-dimethylpiperazinyl, 4-($C_1$–$C_4$)alkoxypiperazinyl, 4-($C_6$–$C_{10}$)aryloxypiperazinyl, 4-hydroxypiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, 2,5-diaza-5,7-dimethylbicyclo[2.2.2]oct-2-yl and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl, 2-($C_1$–$C_3$)alkylthiomorpholinyl and 3-($C_3$–$C_6$)cycloalkylthiomorpholinyl; N-azolyl and substituted N-azolyl group selected from 1-imidazolyl, 2-($C_1$–$C_3$)alkyl-1-imidazolyl, 3-($C_1$–$C_3$)alkyl-1-imidazolyl, 1-pyrazolyl, 2-($C_1$–$C_3$)alkyl-1-pyrrolyl, 3-($C_1$–$C_3$)alkyl-1-pyrazolyl, indolyl, 1-(1,2,3-triazolyl), 4-($C_1$–$C_3$)alkyl-1-(1,2,3-triazolyl), 5-($C_1$–$C_3$)alkyl-1-(1,2,3-triazolyl, 4-(1,2,4-triazolyl), 1-tetrazolyl, 2-tetrazolyl and benzimidazolyl; (heterocycle)amino group selected from 2- or 3-furanylamino, 2- or 3-thienylamino, 2-, 3- or 4-pyridylamino, 2- or 5-pyridazinylamino, 2-pyrazinylamino, 2-(imidazolyl)amino, (benzimidazolyl)amino, and (benzothiazolyl)amino and substituted (heterocycle)amino group as defined above with substitution selected from straight or branched ($C_1$–$C_6$)alkyl; (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino as defined above with substitution selected from straight or branched ($C_1$–$C_6$)alkyl; carboxy($C_2$–$C_4$)alkylamino group selected from aminoacetic acid, α-aminopropionic acid, β-aminopropionic acid, α-butyric acid, and β-aminobutyric acid and the enantiomers of said carboxy-($C_2$–$C_4$)alkylamino group; ($C_1$–$C_4$)alkoxycarbonylamino group selected from methoxycarbonylamino, ethoxycarbonylamino, allyloxycarbonylamino, propoxycarbonylamino, isoproxycarbonylamino, 1,1-dimethylethoxycarbonylamino, n-butoxycarbonylamino, and 2-methylpropoxycarbonylamino; ($C_1$–$C_4$)alkoxyamino group selected from methoxyamino, ethoxyamino, n-propoxyamino, 1-methylethoxyamino, n-butoxyamino, 2-methylpropoxyamino, and 1,1-dimethylethoxyamino; ($C_3$–$C_8$)cycloalkoxyamino group selected from cyclopropoxyamino, trans-1,2-dimethylcyclopropoxyamino, cis-1,2-dimethylcyclopropoxyamino, cyclobutoxyamino, cyclopentoxyamino, cyclohexoxyamino, cycloheptoxyamino, cyclooctoxyamino, bicyclo[2.2.1]hept-2-yloxyamino, bicyclo[2.2.2]oct-2-yloxyamino and the diastereomers and enantiomers of said ($C_3$–$C_8$)cycloalkoxyamino group; ($C_6$–$C_{10}$)aryloxyamino group selected from phenoxyamino, 1-naphthyloxyamino and 2-naphthyloxyamino; ($C_7$–$C_{11}$)arylalkoxyamino group selected from benzyloxyamino, 2-phenylethoxyamino, 1-phenylethoxyaminoamino, 2-(naphthyl)methoxyamino, 1-(naphthyl)methoxyamino and phenylpropoxyamino;

$R^5$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylidazolyl, or a five membered saturated ring with one or two N, O, S or Se heteroatoms and an adjacent appended O heteroatom selected from γ-butyrolactam, γ-butyrolactone, imidazolidinone or N-aminoimidazolidinone, or a six membered aromatic ring with one to three N heteroatoms selected from pyridyl, pyridazinyl, pyrazinyl, sym-triazinyl, unsym-triazinyl, pyrimidinyl or ($C_1$–$C_3$) alkylthiopyridazinyl, or a six membered saturated ring with one or two N, O, S or Se heteroatoms and an adjacent appended O heteroatom selected from 2,3-dioxo-1-piperazinyl, 4-ethyl-2,3dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —($CH_2$)$_n$$COOR^7$ where n=0–4 and $R^7$ is selected from hydrogen; straight or branched ($C_1$–$C_3$)alkyl group selected from methyl, ethyl, n-propyl or 1-methylethyl; or ($C_6$–$C_{10}$)aryl group selected from phenyl, α-naphthyl, or β-naphthyl;

$R^6$ is selected from hydrogen; straight or branched ($C_1$–$C_3$)alkyl group selected from methyl, ethyl, n-propyl or 1-methylethyl; ($C_6$–$C_{10}$)aryl group selected from phenyl, α-naphthyl or β-naphthyl; ($C_7$–$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom selected from γ-butyrolactam, γ-butyrolactone, imidazolidinone or N-aminoimidazolidinone, or a six membered aromatic ring with one to three N heteroatoms selected from pyridyl, pyridazinyl, pyrazinyl, sym-triazinyl, unsymtriazinyl, pyrimidinyl or ($C_1$–$C_3$)alkylthiopyridazinyl, or a six membered saturated ring with one or two N, O, S or Se heteroatoms and an adjacent appended O heteroatom such as 2,3-dioxo-1-piperazinyl, 4-ethyl-2,3-dioxo-1-piperazinyl, 4-methyl-2,3-dioxo-1-piperazinyl, 4-cyclopropyl-2-dioxo-1-piperazinyl, 2-dioxomorpholinyl, 2-dioxothiomorpholinyl; or —($CH_2$)$_n$$COOR^7$ where n=0–4 and $R^7$ is selected from hydrogen; straight or branched ($C_1$–$C_3$)alkyl selected from methyl, ethyl, n-propyl or 1-methylethyl; or ($C_6$–$C_{10}$)aryl selected from phenyl, α-naphthyl or β-naphthyl; with the proviso that $R^5$ and $R^6$ cannot both be hydrogen; or $R^5$ and $R^6$ taken together are —($CH_2$)$_2$B($CH_2$)$_2$—, wherein B is selected from ($CH_2$)$_m$ and m=0–1, —NH, —N($C_1$–$C_3$)alkyl, straight or branched, —N($C_1$–$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

2. The compound according to claim 1, wherein:

X is halogen or trifluoromethanesulfonloxy, the halogen is selected from bromine, chlorine, fluorine and iodine;

R is selected from hydrogen; halogen selected from bromine, chlorine and iodine; or R=—$NR^1R^2$ and when R=—$NR^1R^2$ and $R^1$=hydrogen, $R^2$=methyl, ethyl, n-propyl, 1-methylethyl, n-butyl, 1-methylpropyl or 2-methylpropyl;

and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched ($C_1$–$C_8$)alkyl group selected from methyl, ethyl, propyl, isopropyl, butyl, isobutyl, pentyl, hexyl, heptyl and octyl; α-hydroxy($C_1$–$C_4$)alkyl group selected from hydroxymethyl, α-hydroxyethyl, α-hydroxy-1-methylethyl, α-hydroxypropyl and α-hydroxybutyl; carboxyl($C_1$–$C_8$)alkyl group; ($C_6$–$C_{10}$)aryl group selected from phenyl, α-naphthyl and β-naphthyl; substituted($C_6$–$C_{10}$)aryl group with substitution selected from hydroxy, halogen, ($C_1$–$C_4$)alkoxy, ($C_1$–$C_4$)alkoxycarbonyl, and carboxy; ($C_7$–$C_9$)aralkyl group selected from benzyl, 1-phenylethyl, 2-phenylethyl and phenylpropyl; substituted-($C_7$–$C_9$)aralkyl group with substitution selected from halo, ($C_1$–$C_4$)alkyl, ($C_1$–$C_4$)alkoxy, ($C_1$–$C_4$)alkylsulfonyl, cyano and carboxy;

$R^4$ is selected from hydrogen and ($C_1$–$C_4$)alkyl selected from methyl, ethyl, propyl, isopropyl, butyl and isobutyl;

when $R^3$ does not equal $R^4$ the stereochemistry of the carbon bearing the W substituent may be either the racemate (DL) or the individual enantiomers (L or D);

W is selected from amino; hydroxylamino; ($C_1$–$C_{12}$) straight or branched alkyl monosubstituted amino group with substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-di-methylbutyl, 3-methylpentyl, 1,2-dimethylbutyl, 1,3-di-methylbutyl, 1-methyl-1-ethylpropyl, heptyl, octyl, nonyl, decyl and the diastereomers and enantiomers of said branched alkyl monosubstituted amino group; ($C_3$–$C_8$)cycloalkyl monosubstituted amino group with substitution selected from cyclopropyl, trans-1,2-dimethylcyclopropyl, cis-1,2-dimethylcyclopropyl, cyclobutyl, cyclopentyl, cyclohexyl, cycloheptyl, cyclooctyl, and the diastereomers and enantiomers of said ($C_3$–$C_8$)cycloalkyl monosubstituted amino group; [($C_4$–$C_{10}$)cycloalkyl]alkyl monosubstituted amino group with substitution selected from (cyclopropyl)methyl, (cyclopropyl)ethyl, (cyclobutyl)methyl, (trans-2-methylcyclopropyl)methyl and (cis-2-methylcyclobutyl)methyl; ($C_3$–$C_{10}$)alkenyl monosubstituted amino group with substitution selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; ($C_7$–$C_{10}$)aralkylamino group selected from benzylamino, 2-phenylethylamino, 1-phenylethylamino, 2-(naphthyl)methylamino, 1-(naphthyl)methylamino and phenylpropylamino; straight or branched symmetrical disubstituted ($C_2$–$C_{14}$)alkylamino group substitution selected from dimethyl, diethyl, diisopropyl, di-n-propyl, dibutyl and diisobutyl; symmetrical disubstituted (C$_3$-C$_{14}$)cycloalkylamino group with substitution selected from dicyclopropyl, dicyclobutyl, dicyclopentyl, dicyclohexyl and dicycloheptyl; straight or branched unsymmetrical disubstituted (C$_3$-C$_{14}$)alkylamino group wherein the total number of carbons in the substitution is not more than 14; unsymmetrical disubstituted (C$_4$-C$_{14}$)cycloalkylamino group wherein the total number of carbons in the substitution is not more than 14; (C$_2$-C$_8$)azacycloalkyl and substituted (C$_2$-C$_8$)azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl, 2-azabicyclo[2.1.1]hex-2-yl, 5-azabicyclo[2.1.1]hex-5-yl, 2-azabicyclo[2.2.1]hept-2-yl, 7-azabicyclo[2.2.1]hept-7-yl, 2-azabicyclo[2.2.2]oct-2-yl and the diastereomers and enantiomers of said (C$_2$-C$_8$)azacycloalkyl and substituted (C$_2$-C$_8$)azacycloalkyl group; 1-azaoxacycloalkyl selected from morpholinyl and 1-aza-5-oxocycloheptane; substituted 1-azaoxacycloalkyl group selected from 2-(C$_1$-C$_3$)alkylmorpholinyl, 3-(C$_1$-C$_3$)alkylisoxazolidinyl, tetrahydrooxazinyl and 3,4-dihydrooxazinyl; [1,n]-diazacycloalkyl and substituted [1,n]-diazacycloalkyl group selected from piperazinyl, 2-(C$_1$-C$_3$)alkylpiperazinyl, 4-(C$_1$-C$_3$)alkylpiperazinyl, 2,4-dimethylpiperazinyl, 4-(C$_1$-C$_4$)alkoxypiperazinyl, 2,5-diazabicyclo[2.2.1]-hept-2-yl, 2,5-diaza-5-methylbicyclo[2.2.1]hept-2-yl, 2,3-diaza-3-methylbicyclo[2.2.2]oct-2-yl, and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl, 2-(C$_1$-C$_3$)alkylthiomorpholinyl and 3-(C$_3$-C$_6$)cycloalkylthiomorpholinyl; N-azolyl and substituted N-azolyl group selected from 1-imidazolyl, 2-(C$_1$-C$_3$)alkyl-1-imidazolyl, 3-(C$_1$-C$_3$)alkyl-1-imidazolyl, 1-pyrrolyl, 2-(C$_1$-C$_3$)alkyl-1-pyrrolyl, 3-(C$_1$-C$_3$)alkyl-1-pyrazolyl, indolyl, 1-(1,2,3-triazolyl), 4-(C$_1$-C$_3$)alkyl-1-(1,2,3-triazolyl), 5-(C$_1$-C$_3$)alkyl-1-(1,2,3-triazolyl) and 4-(1,2,4-triazolyl); (heterocycle)methylamino group selected from 2- or 3-furylmethylamino, 2- or 3-thienylmethylamino, 2-, 3- or 4-pyridylmethylamino, 2- or 5-pyridazinylmethylamino, 2-pyrazinylmethylamino, 2-(imidazolyl)methylamino, (benzimidazolyl)methylamino, and (benzothiazolyl)methylamino and substituted (heterocycle)methylamino group as defined above with substitution selected from straight or branched (C$_1$-C$_6$)alkyl; carboxy(C$_2$-C$_4$)alkylamino group selected from aminoacetic acid, α-aminopropionic acid, β-aminopropionic acid, α-butyric acid, β-aminobutyric acid and the enantiomers of said carboxy(C$_2$-C$_4$)alkylamino group; (C$_1$-C$_4$)alkoxycarbonylamino group selected from methoxycarbonylamino, ethoxycarbonylamino, allyloxycarbonylamino, propoxycarbonylamino, isoproproxycarbonylamino, 1,1-dimethylethoxycarbonylamino, n-butoxycarbonylamino, and 2-methylpropoxycarbonylamino; (C$_1$-C$_4$)alkoxyamino group selected from methoxyamino, ethoxyamino, n-propoxyamino, 1-methylethoxyamino, n-butoxyamino, 2-methylpropoxyamino, and 1,1-dimethylethoxyamino; (C$_3$-C$_8$)cycloalkoxyamino group selected from cyclopropoxyamino, trans-1,2-dimethylcyclopropoxyamino, cis-1,2-dimethylcyclopropoxyamino, cyclobutoxyamino, cyclopentoxyamino, cyclohexoxyamino, cycloheptoxyamino, cyclooctoxyamino, bicyclo[2.2.1]hept-2-yloxyamino, bicyclo[2.2.2]oct-2-yloxyamino, and the diastereomers and enantiomers of said (C$_3$-C$_8$)cycloalkoxyamino group; (C$_7$-C$_{11}$)arylalkoxyamino group selected from benzyloxyamino, 2-phenylethoxyamino, 1-phenylethoxyamino, 2-(naphthyl)methoxyamino, 1-(naphthyl)methoxyamino and phenylpropoxyamino;

R$^5$ is selected from hydrogen; straight or branched (C$_1$-C$_3$)alkyl group selected from methyl, ethyl, n-propyl or 1-methylethyl; (C$_6$-C$_{10}$)aryl group selected from phenyl, α-naphthyl or β-naphthyl; (C$_7$-C$_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom selected from γ-butyrolactam, γ-butyrolactone, imidazolidinone or N-aminoimidazolidinone, or a six membered aromatic ring with one to three N heteroatoms selected from pyridyl, pyridazinyl, pyrazinyl, sym-triazinyl, unsymtriazinyl, pyrimidinyl or (C$_1$-C$_3$) alkylthiopyridazinyl; or —(CH$_2$)$_n$COOR$^7$ where n=0-4 and R$^7$ is selected from hydrogen; straight or branched (C$_1$-C$_3$)alkyl group selected from methyl, ethyl, n-propyl or 1-methylethyl; or (C$_6$-C$_{10}$)aryl group selected from phenyl, α-naphthyl, or β-naphthyl;

R$^6$ is selected from hydrogen; straight or branched (C$_1$-C$_3$)alkyl group selected from methyl, ethyl, n-propyl or 1-methylethyl; (C$_6$-C$_{10}$)aryl group selected from phenyl, α-naphthyl or β-naphthyl; (C$_7$-C$_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl, or a five membered saturated ring with one or two N, O, S or Se heteroatoms and an adjacent appended O heteroatom selected from γ-butyrolactam, γ-butyrolactone, imidazolidinone or N-aminoimidazolidinone, or a six membered aromatic ring with one to three N heteroatoms selected from pyridyl, pyridazinyl, pyrazinyl, sym-triazinyl, unsymtriazinyl, pyrimidinyl or ($C_1$-$C_3$)alkylthiopyridazinyl; or —$(CH_2)_n COOR^7$ where n=0-4 and $R^7$ is selected from hydrogen; straight or branched ($C_1$-$C_3$)alkyl selected from methyl, ethyl, n-propyl or 1-methylethyl; or ($C_6$-$C_{10}$)aryl selected from phenyl, α-naphthyl or β-naphthyl; with the proviso that $R^5$ and $R^6$ cannot both be hydrogen;

or $R^5$ and $R^6$ taken together are —$(CH_2)_2 B(CH_2)_2$—, wherein B is selected from $(CH_2)_m$ and m=0-1, —NH, —N($C_1$-$C_3$)alkyl straight or branched, —N($C_1$-$C_4$)alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

3. The compound according to claim 1, wherein:

X is halogen or trifluoromethanesulfonyloxy, the halogen is selected from bromine, chlorine, fluorine and iodine;

R is selected from hydrogen; halogen selected from bromine, chlorine and iodine; or R=—$NR^1R^2$ and when R=—$NR^1R^2$ and $R^1$=hydrogen, $R^2$=methyl, ethyl, n-propyl, 1-methylethyl, n-butyl, 1-methylpropyl, 2-methylpropyl or 1,1-dimethylethyl;

and when $R^1$=methyl or ethyl, $R^2$=methyl, ethyl, n-propyl, 1-methylethyl, n-butyl, 1-methylpropyl or 2-methylpropyl;

$R^3$ is selected from hydrogen; straight or branched ($C_1$-$C_6$)alkyl group selected from methyl, ethyl, propyl, isopropyl, butyl, isobutyl, pentyl and hexyl; ($C_6$-$C_{10}$)aryl group selected from phenyl, α-naphthyl and β-naphthyl; ($C_7$-$C_9$)aralkyl group selected from benzyl, 1-phenylethyl, 2-phenylethyl and phenylpropyl;

$R^4$ is selected from hydrogen and ($C_1$-$C_4$)alkyl selected from methyl, ethyl, propyl, isopropyl, butyl and isobutyl; when $R^3$ does not equal $R^4$ the stereochemistry of the carbon bearing the W substituent may be either the racemate (DL) or the individual enantiomers (L or D);

W is selected from amino; ($C_1$-$C_{12}$) straight or branched alkyl monosubstituted amino group with substitution selected from methyl, ethyl, n-propyl, 1-methylethyl, n-butyl, 1-methylpropyl, 2-methylpropyl, 1,1-dimethylethyl, n-pentyl, 2-methylbutyl, 1,1-dimethylpropyl, 2,2-dimethylpropyl, 3-methylbutyl, n-hexyl, 1-methylpentyl, 1,1-dimethylbutyl, 2,2-dimethylbutyl, 3-methylpentyl, 1,2-dimethylbutyl, 1,3-dimethylbutyl, 1-methyl-1-ethylpropyl and the diastereomers and enantiomers of said branched alkyl monosubstituted amino group; ($C_3$-$C_5$)cycloalkyl monosubstituted amino group with substitution selected from cyclopropyl, trans-1,2-dimethylcyclopropyl, cis-1,2-dimethylcyclopropyl, cyclobutyl and the diastereomers and enantiomers of said ($C_3$-$C_5$)cycloalkyl monosubstituted amino group; [($C_4$-$C_{10}$)cycloalkyl]alkyl monosubstituted amino group with substitution selected from (cyclopropyl)methyl, (cyclopropyl)ethyl and (cyclobutyl)methyl; ($C_3$-$C_{10}$)alkenyl monosubstituted amino group with substitution selected from allyl, 3-butenyl, 2-butenyl (cis or trans), 2-pentenyl, 4-octenyl, 2,3-dimethyl-2-butenyl, 3-methyl-2-butenyl, 2-cyclopentenyl and 2-cyclohexenyl; ($C_7$-$C_{10}$)aralkylamino group selected from benzylamino, 2-phenylethylamino, 1-phenylethylamino, 2-(naphthyl)methylamino, 1-(naphthyl)methylamino and phenylpropylamino; straight or branched symmetrical disubstituted ($C_2$-$C_{14}$)alkylamino group with substitution selected from dimethyl, diethyl, diisopropyl, and di-n-propyl; straight or branched unsymmetrical disubstituted ($C_3$-$C_{14}$)alkylamino group wherein the total number of carbons in the substitution is no more than 14; unsymmetrical disubstituted ($C_4$-$C_{14}$)cycloalkylamino group wherein the total number of carbons in the substitution is no more than 14; ($C_2$-$C_8$)azacycloalkyl and substituted ($C_2$-$C_8$)azacycloalkyl group selected from aziridinyl, azetidinyl, pyrrolidinyl, piperidinyl, 4-methylpiperidinyl, 2-methylpyrrolidinyl, cis-3,4-dimethylpyrrolidinyl, trans-3,4-dimethylpyrrolidinyl and the diastereomers and enantiomers of said ($C_2$-$C_8$)azacycloalkyl and substituted ($C_2$-$C_8$)azacycloalkyl group; 1-azaoxacycloalkyl selected from morpholinyl and 1-aza-5-oxocycloheptane; substituted 1-azaoxacycloalkyl group substitution selected from 2-($C_1$-$C_3$)alkylmorpholinyl, 3-($C_1$-$C_3$)alkylisoxazolidinyl and tetrahydrooxazinyl; [1,n]-diazacycloalkyl and substituted [1,n]-diazacycloalkyl group selected from piperazinyl, 2-($C_1$-$C_3$)alkylpiperazinyl, 4-($C_1$-$C_3$)alkylpiperazinyl, 2,4-dimethylpiperazinyl, 2,5-diazabicyclo[2.2.1]hept-2-yl, 2,5-diaza-5-methylbicyclo[2.2.1]hept-2-yl, 2,3-diaza-3-methylbicyclo[2.2.2]oct-2-yl, and the diastereomers or enantiomers of said [1,n]-diazacycloalkyl and substituted [1,n]-diazacycloalkyl group; 1-azathiacycloalkyl and substituted 1-azathiacycloalkyl group selected from thiomorpholinyl and 2-($C_1$-$C_3$)alkylthiomorpholinyl; N-azolyl and substituted N-azolyl group selected from 1-imidazolyl, indolyl, 1-(1,2,3-triazolyl) and 4-(1,2,4-triazolyl); (heterocycle)methylamino group selected from 2- or 3-furylmethylamino, 2- or 3-thienylmethylamino and 2-, 3- or 4-pyridylmethylamino; ($C_1$-$C_4$)alkoxycarbonylamino group selected from methoxycarbonylamino, ethoxycarbonylamino, allyloxycarbonylamino, propoxycarbonylamino, isoproproxycarbonylamino, 1,1-dimethylethoxycarbonylamino, n-butoxycarbonylamino, and 2-methylpropoxycarbonylamino; ($C_1$-$C_4$)alkoxyamino group selected from methoxyamino, ethoxyamino, n-propoxyamino, 1-methylethoxyamino, n-butoxyamino, 2-methylpropoxyamino, and 1,1-dimethylethoxyamino; ($C_7$-$C_{11}$)arylalkoxyamino group selected from benzyloxyamino, 2-phenylethoxyamino, 1-phenylethoxyamino, 2-(naphthyl)methoxyamino, 1-(naphthyl)methoxyamino and phenylpropoxyamino;

$R^5$ is selected from hydrogen; straight or branched ($C_1$-$C_3$)alkyl group selected from methyl, ethyl, n-propyl or 1-methylethyl; ($C_6$-$C_{10}$)aryl group selected from phenyl, α-naphthyl or β-naphthyl; ($C_7$-$C_9$)aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; or $-(CH_2)_nCOOR^7$ where n=0-4 and $R^7$ is selected from hydrogen; straight or branched $(C_1-C_3)$alkyl group selected from methyl, ethyl, n-propyl or 1-methylethyl; or $(C_6-C_{10})$aryl group selected from phenyl, α-naphthyl, or β-naphthyl;

$R^6$ is selected from hydrogen; straight or branched $(C_1-C_3)$alkyl group selected from methyl, ethyl, n-propyl or 1-methylethyl; $(C_6-C_{10})$aryl group selected from phenyl, α-naphthyl or β-naphthyl; $(C_7-C_9)$aralkyl group selected from benzyl, 1-phenylethyl, 2-phenylethyl or phenylpropyl; a heterocycle group selected from a five membered aromatic or saturated ring with one N, O, S or Se heteroatom optionally having a benzo or pyrido ring fused thereto selected from pyrrolyl, N-methylindolyl, indolyl, 2-pyrrolidinyl, 3-pyrrolidinyl, 2-pyrrolinyl, tetrahydrofuranyl, furanyl, benzofuranyl, tetrahydrothienyl, thienyl, benzothienyl or selenazolyl, or a five membered aromatic ring with two N, O, S or Se heteroatoms optionally having a benzo or pyrido ring fused thereto selected from imidazolyl, pyrazolyl, benzimidazolyl, oxazolyl, benzoxazolyl, indazolyl, thiazolyl, benzothiazolyl, 3-alkyl-3H-imidazo[4,5-b]pyridyl or pyridylimidazolyl; or $-(CH_2)_nCOOR^7$ where n=0-4 and $R^7$ is selected from hydrogen; straight or branched $(C_1-C_3)$alkyl selected from methyl, ethyl, n-propyl or 1-methylethyl; or $(C_6-C_{10})$aryl selected from phenyl, α-naphthyl or β-naphthyl; with the proviso that $R^5$ and $R^6$ cannot both be hydrogen;

or $R^5$ and $R^6$ taken together are $-(CH_2)_2B(CH_2)_2-$, wherein B is selected from $(CH_2)_m$ and m=0-1, $-NH$, $-N(C_1-C_3)$alkyl, straight or branched, $-N(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

4. The compound according to claim 1, wherein:

X is halogen or trifluoromethanesulfonyloxy, the halogen is selected from chlorine and fluorine; R is selected from hydrogen; halogen selected from chlorine and iodine; or $R=-NR^1R^2$ and when $R=-NR^1R^2$ and $R^1$=methyl or ethyl, $R^2$=methyl and ethyl;

$R^3$ is selected from hydrogen; straight or branched $(C_1-C_2)$alkyl group selected from methyl and ethyl;

$R^4$ is selected from hydrogen and $(C_1-C_6)$alkyl selected from methyl and ethyl;

when $R^3$ does not equal $R^4$ the stereochemistry of the carbon bearing the W substituent may be either the racemate (DL) or the individual enantiomers (L or D);

W is selected from amino; $(C_1-C_4)$ straight or branched alkyl monosubstituted amino group with substitution selected from methyl, ethyl, n-propyl, 1-methylethyl, n-butyl and 1-methylpropyl; $(C_3-C_4)$cycloalkyl monosubstituted amino group with substitution selected from cyclopropyl and cyclobutyl; $(C_4-C_5)$azacycloalkyl and substituted azacycloalkyl selected from pyrrolidinyl, piperidinyl, 4-methylpiperidinyl; 1-azaoxacycloalkyl selected from morpholinyl; [1,n]-diazacycloalkyl and substituted [1,n]-diazacycloalkyl group selected from piperazinyl and 4-$(C_1-C_3)$alkylpiperazinyl; N-azolyl and substituted N-azolyl group selected from 1-imidazolyl, 2-$(C_1-C_3)$alkyl-1-imidazolyl and 3-$(C_1-C_3)$alkyl-1-imidazolyl; (heterocycle)methylamino group selected from 2-, 3- or 4-pyridylmethylamino; carboxy$(C_2-C_4)$alkylamino group selected from aminoacetic acid, α-aminopropionic acid, β-aminopropionic acid, α-butyric acid, β-aminobutyric acid and the enantiomers of said carboxy$(C_2-C_4)$alkylamino group;

$R^5$ is selected from hydrogen; straight or branched $(C_1-C_3)$alkyl group selected from methyl, ethyl, n-propyl or 1-methylethyl;

$R^6$ is selected from hydrogen; straight or branched $(C_1-C_3)$alkyl group selected from methyl, ethyl, n-propyl or 1-methylethyl; with the proviso that $R^5$ and $R^6$ cannot both be hydrogen;

or $R^5$ and $R^6$ taken together are $-(CH_2)_2B(CH_2)_2-$, wherein B is selected from $(CH_2)_m$ and m=0-1, $-NH$, $-N(C_1-C_3)$alkyl, straight or branched, $-N(C_1-C_4)$alkoxy, oxygen, sulfur or substituted congeners selected from (L or D)proline, ethyl(L or D)prolinate, morpholine, pyrrolidine or piperidine; and the pharmacologically acceptable organic and inorganic salts or metal complexes.

5. The compound according to claim 1 wherein said inorganic salts comprise: hydrochloric, hydrobromic, hydroiodic, phosphoric, nitric or sulfate.

6. The compound according to claim 1 wherein said organic salts comprise: acetate, benzoate, citrate, cysteine or other amino acid, fumarate, glycolate, maleate, succinate, tartrate, alkylsulfonate or arylsulfonate.

7. The compound according to claim 1 wherein said metal complexes comprise: aluminum, calcium, iron, magnesium, manganese and complex salts.

8. A compound according to claim 1, [4S-(4α,12aα)]-8-Chloro-4-(dimethylamino)-9-[[(dimethylamino)acetyl]amino]-1,4,4a,5,5a,-6,11,12a-octahydro-3,10,12,12a-tetrahydroxy-1,11-dioxo-2-naphthacenecarboxamide disulfate.

9. A compound according to claim 1, [4S-(4α,12aα)]-8-Chloro-4-(dimethylamino)-9-[[(dimethylamino)acetyl]amino]-1,4,4a,5,5a,-6,11,12a-octahydro-3,10,12,12a-tetrahydroxy-1,11-dioxo-2-naphthacenecarboxamide.

10. A compound according to claim 1, [4S-(4α,12aα)]-8-Chloro-4,7-(dimethylamino)-9-[[(dimethylamino)acetyl]amino]-1,4,4a,5,5a,6,11,-12a-octahydro-3,10,12,12a-tetrahydroxy-1,11-dioxo-2-naphthacenecarboxamide.

11. A compound according to claim 1, [4S-(4α,12aα)]-9-[[(Butylamino)acetyl]amino]-8-chloro-4,7-bis(-dimethylamino)-1,4,4a,5,5a,6,11,12a-octahydro-3,10,12,12a-tetrahydroxy-1,11-dioxo-2-naphthacenecarboxamide.

12. A compound according to claim 1, [4S-(4α, 12-aα)]-8-Chloro-4,7-bis(dimethylamino)-1,4,4a,5,5a,6,11,-12a-octahydro-3,10,12,12a-tetrahydroxy-9-[[[(3-methylcyclobutyl)amino]acetyl]amino]-1,11-dioxo-2-naphthacenecarboxamide.

13. A compound according to claim 1, [7S-(7α,10aα)]-N-[9-(Aminocarbonyl)-3-chloro-4,7-bis(dimethylamino)-5,5a,6,6a,7,10,10a,12-octahydro-1,8,-10a,11- tetrahydroxy-10,12-dioxo-naphthacenyl]-1H-pyrrole-1-acetamide.

14. A compound according to claim 1, [4S-(4a,12aα)]-8-Chloro-4,7-bis(dimethylamino)-9-[[[(1,1-dimethylethyl)amino]acetyl]amino]-1,4,4a,5,5a,6,11,12a-octahydro-3,10,12,12a-tetrahydroxy-1,11-dioxo-2-naphthacenecarboxamide.

15. A compound according to claim 1, [4S-(4α,12aα)]-8-Chloro-9-[[(cyclopropylamino)acetyl]amino]-4,7-bis(dimethylamino)-1,4,4a,5,5a,6,11,12a-octahydro-3,10,12,12a-tetrahydroxy-1,11-dioxo-2-naphthacenecarboxamide.

16. A compound according to claim 1, [4S-(4α,12aα)]-8-Chloro-9-[[[(cyclobutyloxy)amino]acetyl]amino]-4,7-bis(dimethylamino)-1,4,4a,5,5a,6,-11,12a-octahydro-3,10,12,12a-tetrahydroxy-1,11-dioxo-2-naphthacenecarboxamide.

17. A compound according to claim 1, [7S-(7α,10aα)]-N-[9-(Aminocarbonyl)-3-chloro-4,7-bis(dimethylamino)-5,5a,6,6a,7,10,10a,12-octahydro-1,8,-10a,11-tetrahydroxy-10,12-dioxo-2-naphthacenyl]-1-pyrrolidineacetamide.

18. A compound according to claim 1, [7S-(7α,10aα)]-N-[9-(Aminocarbonyl)-3-chloro-4,7-bis(dimethylamino)-5,5a,6,6a,7,10,10a,12-octahydro-1,8,9,10a,11-tetrahydroxy-10,12-dioxo-2-naphthacenyl]-(3-methyl-1-pyrrolidine)acetamide.

19. A compound according to claim 1, [4S-(4α,12aα)]-8-Chloro-4,7-bis(dimethylamino)-1,4,4a,5,-,5a,6,11,12a-octahydro-3,10,12,12a-tetrahydroxy-1,11-dioxo-9-[[(propylamino)acetyl]amino]-2-naphthacenecarboxamide.

20. A compound according to claim 1, [4S-(4α,12aα)]-8-Chloro-4,7-Bis(dimethylamino)-1,4,4a,5,5a,6,11,-12a-octahydro-3,10,12,12a-tetrahydroxy-1,11-dioxo-9-[[1-oxo-2-(propylamino)propyl]amino]-2-naphthacenecarboxamide.

21. A compound according to claim 1, [7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-α-cyclobutyltetrahydro-2H-1,2-isoxazine-2-acetamide.

22. A compound according to claim 1, [4S-(4α,12aα)]-8-Chloro-4,7-bis(dimethylamino)-1,4,4a,5,5a,6,11,12a-octahydro-3,10,12,12a-tetrahydroxy-1,11-dioxo-9-[[phenyl[(phenylmethyl)amino]acetyl]amino]-2-naphthacenecarboxamide.

23. A compound according to claim 1, [7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-α-cyclopropyl-α-methyl-1-azetidineacetamide.

24. A compound according to claim 1, [7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-α-(1,1-dimethylethyl)-(3-methyl-4-morpholine)acetamide.

25. A compound according to claim 1, [4S-(4α,12aα)]-8-Chloro-9-[[(2,4-difluorophenyl)[(2-phenylethyl)amino]acetyl]amino]-4,7-bis(dimethylamino)-1,4,4a,5,-,5a,6,11,12a-octahydro-3,10,12,12a-tetrahydroxy-1,11-dioxo-2-naphthacenecarboxamide.

26. A compound according to claim 1, [7S-(7α,10aα)]-N-[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]-α-(methoxyamino)-α-methyl-2-furanacetamide.

27. A compound according to claim 1, [7S-(7α,10aα)]-4-[[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]amino-3-[(1,1-dimethylethyl)amino]-4-oxobutanoic acid methyl ester.

28. A compound according to claim 1, [7S-(7α,10aα)]-4-[[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]amino]-3-(dimethylamino)-4-oxobutanoic acid methyl ester.

29. A compound according to claim 1, [7S-(7α,10aα)]-γ-[[[9-(Aminocarbonyl)-3-chloro-4,7-bis(dimethylamino)-5,5a,6,6a,7,10,10a,12-octahydro-1,8,10a,11-tetrahydroxy-10,12-dioxo-2-naphthacenyl]amino]carbonyl]-1-pyrrolidinebutanoic acid methyl ester.

30. A compound according to claim 1, [4S-(4α,12aα)]-4,7-Bis(Dimethylamino)-9-[[(dimethylamino)acetyl]amino]-8-fluoro-1,4,4a,5,5a,6,11,12a-octahydro-3,10,12,12a-tetrahydroxy-1,11-dioxo-2-naphthacenecarboxamide.

31. A compound according to claim 1, [4S-(4α,12aα)]-9-[[(Butylamino)acetyl]amino]-8-chloro-4-(dimethylamino)-1,4,4a,5,5a,6,11,12a-octahydro-3,10,12,12a-tetrahydroxy-1,11-dioxo-2-naphthacenecarboxamide dihydrochloride.

32. A compound according to claim 1, which is [4S-(4α,12aα)]-8-Chloro-4-(dimethylamino)-1,4,4a,5,-,5a,6,11,12a-octahydro-3,10,12,12a-tetrahydroxy-1,11-dioxo-9-[[(propylamino)acetyl]amino]-2-naphthacenecarboxamide dihydrochloride.

33. A compound according to claim 1, [4S-(4α,12aα)]-8-Chloro-4-(dimethylamino)-1,4,4a,5,5a,6,11,12a-octahydro-3,10,12,12a-tetrahydroxy-1,11-dioxo-9-[[(pentylamino)acetyl]amino]-2-naphthacenecarboxamide dihydrochloride.

34. A compound according to claim 1, [4S-(4α,12aα)]-8-Chloro-4-(dimethylamino)-1,4,4a,5,5a,6,11,12a-octahydro-3,10,12,12a-tetrahydroxy-1,11-dioxo-9-[[(methylamino)acetyl]amino]-2-naphthacenecarboxamide dihydrochloride.

35. A compound according to claim 1, [4S-(4α,12aα)]-8-Chloro-9-[[(cyclopropylmethylamino)acetyl]amino]-4-(dimethylamino)-1,4,4a,5,5a,6,11,12a-octahydro-3,10,12,12a-tetrahydroxy-1,11-dioxo-2-naphthacenecarboxamide dihydrochloride.

36. A compound according to claim 1, [7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-1-pyrrolidineacetamide dihydrochloride.

37. A compound according to claim 1, [7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-1-piperidineacetamide dihydrochloride.

38. A compound according to claim 1, 7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-5-azabicyclo[2.1.1]hexane-5-acetamide dihydrochloride.

39. A compound according to claim 1, [4S-(4α,12aα)]-8-Chloro-9-[[(cyclobutylamino)acetyl]amino]-4-(dimethylamino)-1,4,4a,5,5a,6,11,12a-octahydro-3,10,12,12a-tetrahydroxy-1,11-dioxo-2-naphthacenecarboxamide dihydrochloride.

40. A compound according to claim 1, [7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-α-ethyl-1H-imidazole-1-acetamide dihydrochloride.

41. A compound according to claim 1, [4S-(4α,12aα)]-8-Chloro-9-[[2-(diethylamino)-1-oxopropyl]amino]-4-(dimethylamino)-1,4,4a,5,5a,6,11,12a-octahydro-3,10,12,12a-tetrahydroxy-1,11-dioxo-2-naphthacenecarboxamide.

42. A compound according to claim 1, [7S-(7α,10aα)]-1-[2-[[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]amino]-1-methyl-2-oxoethyl] proline methyl ester.

43. A compound according to claim 1, [7S-(7α,10aα)]-N-[9-(Aminocarbonyl)-3-chloro-7-(dimethylamino)-5,5a,6,6a,7,10,10a,12-octahydro-1,8,10a,11-tetrahydroxy-10,12-dioxo-2-naphthacenyl]-α-(4-hydroxyphenyl)-6-methyl-2,6-diazabicyclo[2.1.1]heptane-2-acetamide.

44. A compound according to claim 1, [4S-(4α,12aα)]-8-Chloro-4-(dimethylamino)-9-[[(dimethylamino)(2-fluorophenyl)acetyl]amino]-1,4,4a,5,5a,6,11,12a-octahydro-3,10,12,12a-tetrahydroxy-1,11-dioxo-2-naphthacenecarboxamide.

45. A compound according to claim 1, [4S-(4α,12aα)]-8-Chloro-4-(dimethylamino)-1,4,4a,5,5a,6,11,12a-octahydro-3,10,12,12a-tetrahydroxy-9-[[1-(4-methoxy-1-piperazinyl)-4-pentenoyl]amino]-1,11-dioxo-2-naphthacenecarboxamide.

46. A compound according to claim 1, [4S-(4α,12aα)]-8-Chloro-4-(dimethylamino)-1,4,4a,5,5a,6,11,12a-octahydro-3,10,12,12a-tetrahydroxy-1,11-dioxo-9-[[1-oxo-4-phenyl-2-[(phenylmethoxy)amino]-butyl]amino]-2-naphthacenecarboxamide.

47. A compound according to claim 1, [7S-(7α,10aα)]-N-[9-(Aminocarbonyl)-3-chloro-7-(dimethylamino)-5,5a,6,6a,7,10,10a12-octahydro-1,8,10a,11-tetrahydroxy-10,12-dioxo-2-naphthacenyl]-α-4-pyridyl-5-azabicyclo[2.1.1]hexan-5-acetamide.

48. A compound according to claim 1, [4S-(4α,12aα)]-4-(Dimethylamino)-9-[[(dimethylamino)acetyl]amino]-8-fluoro-1,4,4a,5,5a,6,11,12a-octahydro-3,10,12,12a-tetrahydroxy-1,11-dioxo-2-naphthacenecarboxamide.

49. A compound according to claim 1, [4S-(4α,12aα)]-4-(Dimethylamino)-8-fluoro-1,4,4a,5,5a,6,11,12a-octahydro-3,10,12,12a-tetrahydroxy-1,11-dioxo-9-[[(propylamino)acetyl]amino]-2-naphthacenecarboxamide.

50. A compound according to claim 1, [4S-(4α,12aα)]-4-(Dimethylamino)-9-[[(dimethylamino)acetyl]amino]-1,4,4a,5,5a,6,11,12a-octahydro-3,10,12,12a-tetrahydroxy-1,11-dioxo-8-[[(trifluoromethyl)sulfonyl]oxy]-2-naphthacenecarboxamide.

51. A pharmaceutical composition of matter comprising a pharmacologically effective amount of a compound according to claim 1 in association with a pharmaceutically acceptable carrier.

* * * * *